(12) United States Patent
Legendre et al.

(10) Patent No.: US 8,758,215 B2
(45) Date of Patent: Jun. 24, 2014

(54) APPLICATOR AND A SET INCLUDING SUCH AN APPLICATOR

(75) Inventors: Jean-Yves Legendre, Paris (FR); Jean Scot, Claye Souilly (FR)

(73) Assignee: L'Oreal, Paris (FR)

(*) Notice: Subject to any disclaimer, the term of this patent is extended or adjusted under 35 U.S.C. 154(b) by 458 days.

(21) Appl. No.: 12/818,891

(22) Filed: Jun. 18, 2010

(65) Prior Publication Data

US 2011/0015463 A1 Jan. 20, 2011

Related U.S. Application Data

(60) Provisional application No. 61/221,330, filed on Jun. 29, 2009.

(30) Foreign Application Priority Data

Jun. 18, 2009 (FR) ...................................... 09 54116

(51) Int. Cl.
*A61M 35/00* (2006.01)

(52) U.S. Cl.
USPC .................................. 600/9; 604/20; 604/22

(58) Field of Classification Search
CPC .................... A61N 5/0616; A61N 2005/0654; A61N 5/062; A61N 1/322; A61N 1/328; A61N 2005/0659; A61N 2005/0663; A61N 2007/0034; A61N 5/06; A61H 2201/10; A61H 7/005; A61H 2039/005; A61H 2201/105
USPC ........................... 600/9, 13–15; 128/897–899
See application file for complete search history.

(56) References Cited

U.S. PATENT DOCUMENTS

| 4,291,685 | A | * | 9/1981 | Taelman .......................... 601/17 |
| 2003/0103930 | A1 | | 6/2003 | Uchida et al. |
| 2003/0108502 | A1 | | 6/2003 | Uchida et al. |
| 2004/0022823 | A1 | | 2/2004 | Uchida et al. |
| 2004/0028711 | A1 | | 2/2004 | Uchida et al. |
| 2004/0030325 | A1 | | 2/2004 | Cahir et al. |

(Continued)

FOREIGN PATENT DOCUMENTS

| EP | 0 218 200 A2 | 4/1987 |
| EP | 0 218 200 A3 | 4/1987 |

(Continued)

OTHER PUBLICATIONS

ICI Americas Inc., "The HLB System, A Time-Saving Guide to Emulsifier Selection", © 1976 ICI Americas Inc., Revised Aug. 1984, 21 Pages.

(Continued)

*Primary Examiner* — Christine Matthews
*Assistant Examiner* — Joshua D Lannu
(74) *Attorney, Agent, or Firm* — Oblon, Spivak, McClelland, Maier & Neustadt, L.L.P.

(57) ABSTRACT

A device for treating human keratinous materials includes an electrical appliance comprising a handpiece and a reader, and an applicator suitable for being removably fastened on the handpiece. The applicator includes a solid cosmetic or dermatological composition for applying to the keratinous materials, and/or an applicator element including fibers and/or cells suitable for enabling a cosmetic or dermatological composition to be applied on keratinous materials. The applicator also includes an encoder for encoding information arranged to be read by the reader. The operation of the handpiece depends on the information read.

20 Claims, 3 Drawing Sheets

(56) References Cited

U.S. PATENT DOCUMENTS

| | | | |
|---|---|---|---|
| 2004/0078278 A1 | 4/2004 | Dauga et al. | |
| 2004/0133251 A1 | 7/2004 | Altshuler et al. | |
| 2004/0147984 A1* | 7/2004 | Altshuler et al. | 607/88 |
| 2006/0236913 A1 | 10/2006 | Wills | |
| 2007/0185553 A1* | 8/2007 | Kennedy | 607/100 |
| 2007/0198004 A1 | 8/2007 | Altshuler et al. | |
| 2007/0254825 A1 | 11/2007 | Shannon et al. | |
| 2008/0262414 A1* | 10/2008 | Barsness et al. | 604/20 |
| 2008/0300529 A1 | 12/2008 | Reinstein | |
| 2009/0118684 A1 | 5/2009 | Da Silva et al. | |

FOREIGN PATENT DOCUMENTS

| | | |
|---|---|---|
| EP | 0 796 861 A1 | 9/1997 |
| EP | 0 899 330 A1 | 3/1999 |
| EP | 0 903 342 A1 | 3/1999 |
| EP | 1 345 919 | 9/2003 |
| FR | 2 466 492 A1 | 4/1981 |
| WO | WO 97/25970 A1 | 7/1997 |
| WO | WO 97/35842 A1 | 10/1997 |
| WO | WO 02/44317 A2 | 6/2002 |
| WO | WO 02/44317 A3 | 6/2002 |
| WO | WO 02/051828 A2 | 7/2002 |
| WO | WO 02/051828 A3 | 7/2002 |
| WO | WO 02/092050 A2 | 11/2002 |
| WO | WO 02/092050 A3 | 11/2002 |
| WO | WO 2007/147731 A2 | 12/2007 |

OTHER PUBLICATIONS

French Preliminary Search Report and Written Opinion completed on Feb. 11, 2010 in corresponding French Application No. 0954116.

* cited by examiner

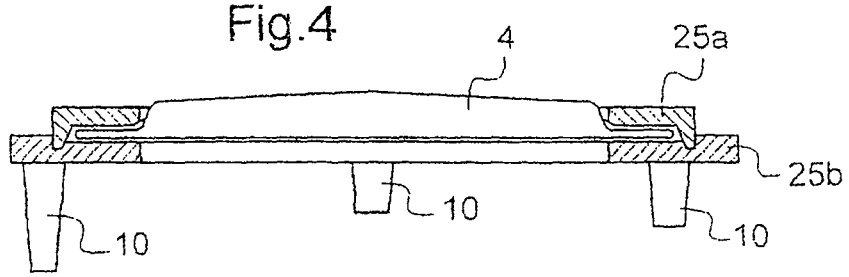
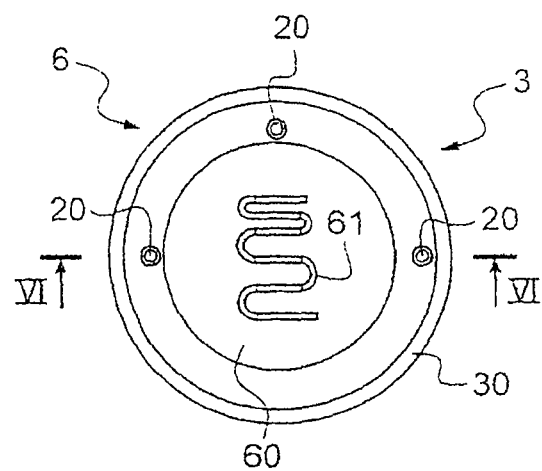
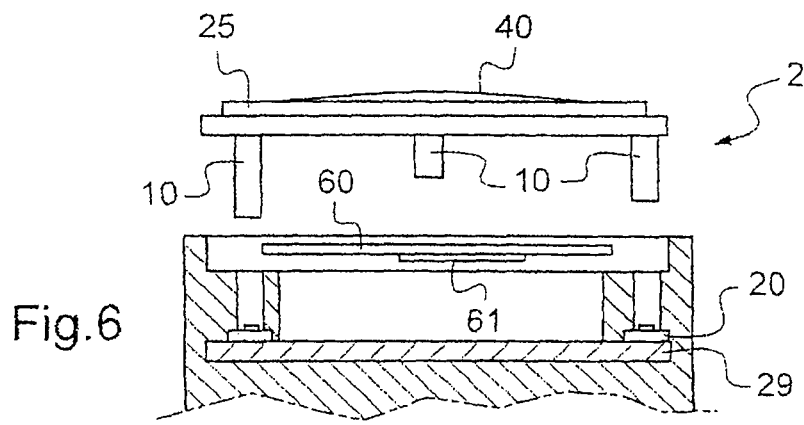

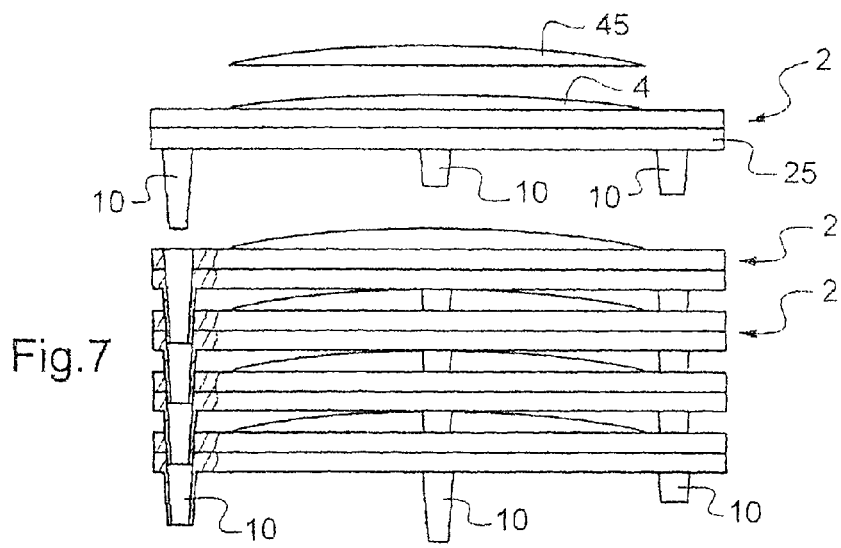
Fig.7
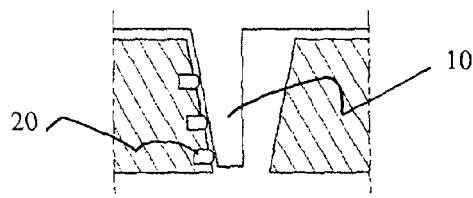
Fig.8a
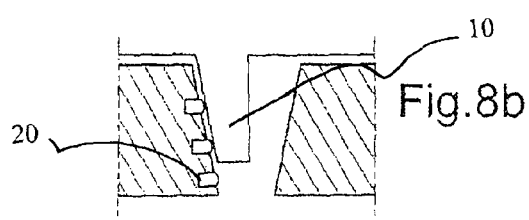
Fig.8b
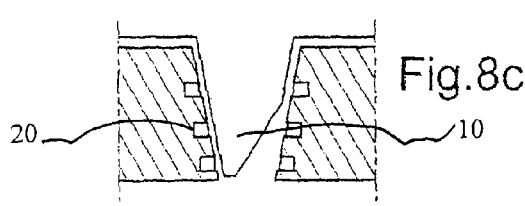
Fig.8c
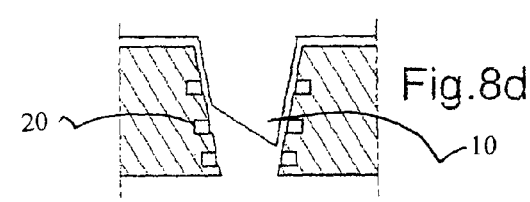
Fig.8d
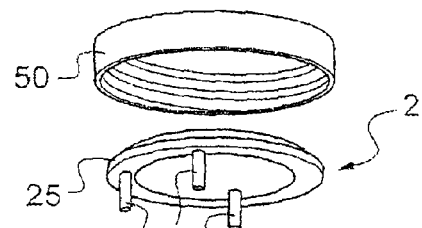
Fig.9
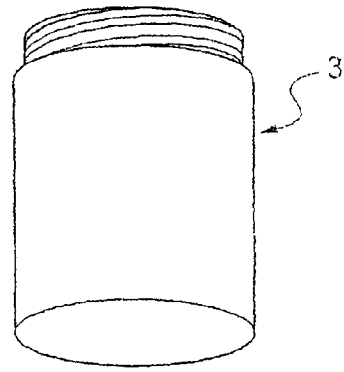

APPLICATOR AND A SET INCLUDING SUCH AN APPLICATOR

FIELD OF THE INVENTION

The present invention relates to applicators and electrical appliances for applying a composition on human keratinous materials, e.g. a therapeutic or cosmetic composition, including makeup or a skin care product.

BACKGROUND OF THE INVENTION

The term "cosmetic composition" designates a product as defined in European Directive 76/768/EEC.

By way of example, it may comprise a composition for application to the skin, the mucous membranes, or to keratinous fibers, e.g. for application to the hair, the scalp, the face, the neck, the forehead, the mouth, the lips, the nose, the outline of the eyes, the chin, the cheeks, the torso, the bust, the back, the stomach, the arms, the legs, the hands, the feet, the elbows, the knees, or the buttocks.

By way of example, the composition may seek to improve the appearance, the radiance, and the texture of the skin, in particular the moisture content, the firmness, the softness, the flexibility, and the elasticity of the skin. The composition may be a cleaning composition.

Compositions for application to human keratinous materials may be presented in the form of liquids, in particular lotions, creams, or gels, that may, under certain circumstances, be for application by means of a medium. There also exist cosmetic compositions that are pre-impregnated in media, such as towelettes or patches, as described for example in applications WO 2002/092050 or WO 2002/44317.

The way in which the composition is applied may play a role in obtaining a satisfactory result.

Thus, it is known that heat can improve the effectiveness with which the skin is cleaned.

For this purpose, compositions have been proposed that contain anhydrous salts, such as magnesium sulfate, that generate an exothermal reaction on contact with the skin. Such compositions are described in US 2003/0103930, US 2003/0108502, US 2004/0022823, and US 2004/0028711. Nevertheless, the heat that is generated is short-lived and the increase in cleaning effectiveness remains small.

Towelettes including non-ionic surfactants have also been proposed in publication US 2007/0254825, with a relatively modest rise in temperature on contact with water.

As disclosed in WO 2007/147731, there exist systems that diffuse hot steam on one face, and that present an endpiece impregnated with cosmetic composition on the other face, without the application of the composition accompanying the application of steam.

It is also known to cool the skin during certain treatments including the application of a composition on the skin. Thus, application US 2008/0300529 describes a Peltier effect applicator that is capable of generating hot or cold temperatures.

US 2007/0185553 discloses a treatment appliance having a removable head that is recognized by a processor. Containers containing different compositions are also recognized automatically.

US 2009/0118684 describes an appliance used to bring an applicator to a desired temperature before it is fitted on a handpiece. The applicator may include a code informing the appliance of an optimum temperature.

There exists a need to further improve applicators for applying a composition on human keratinous materials, in particular a skin cleaning composition.

OBJECT AND SUMMARY OF THE INVENTION

Exemplary embodiments of the invention provide a device for treating human keratinous materials, the device comprising:
  an electrical appliance comprising a handpiece and a reader; and
  an applicator suitable for being removably fastened on the handpiece and comprising:
    i) a solid cosmetic or dermatological composition for applying to the keratinous materials, and/or an applicator element including fibers and/or cells suitable for enabling a cosmetic or dermatological composition to be applied on keratinous materials; and
    ii) an encoder for encoding information arranged to be read by the reader;
  the operation of the handpiece depending on the information read.

The electrical appliance may comprise the handpiece on its own, with the reader being incorporated in the handpiece. The electrical appliance may also comprise the handpiece connected via a wire or wireless connection to a base station, the base station possibly including the reader.

The handpiece may include a module that transmits a stimulus to the applicator as a function of the information read, e.g. heat to a temperature and/or for a duration that depend(s) on the information read. The module moves together with the handpiece during the treatment.

The invention enables the same handpiece to be used with a plurality of different applicators, corresponding to different treatments, to different stages of the same treatment, and/or to different compositions.

The invention thus makes it possible to benefit automatically from a treatment and an applicator that provide high performance for the looked-for effect while retaining great flexibility in use.

The invention may enable heat to be applied together with a composition and may enable the effectiveness of the composition to be improved.

The applicator element may include fibers, e.g. natural or synthetic bristles in particular, in the form of flocking, a felt, a fiber substrate such as a woven or non-woven fabric, a foam of ragged cells, . . . , this list not being limiting. The fibers may be bonded together, as in a woven or non-woven fabric, or non-bonded, as with bristles or flocking.

The above-mentioned cells may stem for example from using a cellular material such as a foam. The greatest dimension of a cell may for example be less than or equal to 3 millimeters (mm), or 1 mm or 0.5 mm. The cells may communicate with one another in all directions when using an open-celled foam, for example.

The applicator element may include cells, e.g. being constituted by a foam having cells that are open, semi-open, or closed.

The handpiece may include a face for transmitting heat and/or energy other than heat energy, in contact with the applicator, and in particular with the composition or the applicator element.

The handpiece may be configured to be easily handled by a user in one hand.

Other exemplary embodiments of the invention provide a method of cosmetic or therapeutic treatment by means of a device as defined above comprising: fastening the applicator on the handpiece;

reading information associated with the applicator; and operating the handpiece as a function of the information read.

Removable Fastening

The applicator includes suitable fastener means for fastening the applicator on the handpiece. The fastener means may form part of the handpiece, part of the applicator, or they may form part both of the handpiece and of the applicator.

The handpiece may include a removable part that is arranged to surround and/or cover at least part of the applicator so as to fasten it on the handpiece.

The fastener may form part of the encoder or of the reader.

In particular exemplary embodiments, the applicators are stackable.

Encoder

The encoder may serve to fasten the applicator on the handpiece.

The encoder may encode at least one operating parameter of the handpiece, in particular a temperature, a treatment time, an energy level, or an identifier of the applicator and/or of the composition.

The encoder may encode at least one item of information relating to the nature of the energy to be applied, e.g. heat energy, ultrasound energy, radiofrequency energy, light energy, this list not being limiting.

The encoder may comprise a single element or optionally it may comprise a plurality of coder elements.

The encoder may comprise at least one of: a magnetic code, an optical code, a bar code, a radiofrequency identification (RFID) chip, an electronic chip, a tactile code, or an electrical code.

By way of example, the encoder may be carried by or formed by one or more portions in relief. The encoder may comprise tabs, e.g. tabs used for fastening the applicator on the handpiece. The coding may depend for example on the presence or the absence of said tabs. In a variant, the coding may depend on the shape or the length of the tabs.

The applicator may include a frame on which the encoder is positioned. The frame may serve as a support for the applicator element.

Independently of the nature of the encoder, the frame may comprise two portions that overlap at least in part and that hold the applicator element between them.

The encoder may be made together with the frame, e.g. being molded integrally therewith. For example, it may comprise tabs or other portions in relief for co-operating with the handpiece.

In particular exemplary embodiments, the fastener of the applicator coincides with the encoder.

The applicator may include two optionally identical opposite sides, at least one of which defines the base that is used for application.

In particular exemplary embodiments, the two sides of the applicator are different, and the applicator is arranged to be fastened on the handpiece using one side only. In a variant, the applicator may be fastened on one side or the other.

The applicator may present two opposite faces having different application characteristics, e.g. different roughnesses, porosities, or thicknesses, thus enabling two different types of application to be performed, depending on the face selected by the user, and the handpiece may recognize which face is in use, e.g. by encoders that differ between the faces.

The applicator may be contained in sealed packaging prior to being mounted on the handpiece.

Prior to being used, the applicator may have a membrane seal, e.g. a film heat-sealed on the above-mentioned frame. The membrane may include a layer of metal, e.g. of aluminum, so as to improve conservation of the composition and/or so as to facilitate the operation of heat-sealing on the frame.

The frame may include a plurality of thicknesses of different materials that are assembled together.

The applicator may be of any shape. When observed in face view, it may present an outline that is optionally circular, e.g. the outline may be oval or polygonal.

The applicator may be for single use. The applicator may be designed for some predefined maximum number of applications. The encoder may store information relating to the maximum possible number of uses, and optionally the number of uses that have already been performed.

The encoder may comprise read-only means. The encoder may be accessible for reading and writing, e.g. when using an electronic chip.

Reader

The encoder is arranged to co-operate with a reader of the appliance, the reader possibly being present in the handpiece.

The reader may provide control logic, e.g. a microprocessor, information useful for treatment, e.g. information useful for determining a temperature or an energy level for the handpiece during treatment.

The reader may be a single sensor, or may comprise a plurality of sensors.

The reader may comprise at least one sensor taken from the following list: tactile feeler, optical reader, electrical sensors, mechanical or optoelectronic switches, magnetic reader, bar code reader, RFID reader.

The reader may co-operate contactlessly with the encoder, in particular when using an RFID chip.

The reader may form a part of a fastener of the applicator to the handpiece. In particular exemplary embodiments, the fastener is the same as the reader. For example, a switch used as reader may snap-fasten onto a tab of the applicator engaged on the handpiece.

The reader may comprise read/write means. In particular exemplary embodiments, information concerning the number of uses already performed and/or the number of uses that are still possible is read by the reader and is updated in a write operation. By way of example, this may serve to check that the applicator is not out-of-date and to warn the user when it is necessary to replace the applicator. The term "out-of-date" means an applicator for which no use is still possible.

The operation of the handpiece depends on reading the encoder of the applicator. For example, the handpiece may be arranged to be incapable of being set into operation in the absence of an applicator or in the presence of an applicator that cannot be read or that is poorly fastened or that must not be used any more.

The appliance may be configured to prevent reuse of an applicator once it has been used in predefined conditions. For example, the appliance may remember a number of uses and/or a duration of use and may compare said value with a predefined threshold, which threshold may depend on the applicator. For example, each applicator encodes information informing the appliance about the maximum number or duration of uses. The appliance may be arranged to measure duration of use.

The handpiece may include a system for locking the applicator on the handpiece so as to prevent the user removing the applicator until some predefined condition is satisfied, e.g. switching off the handpiece. The locking system may be actuated by an electromagnet, for example, and it may optionally engage a tab used for encoding the information.

The appliance may be started manually or automatically, for example it may start when the applicator is put into place. The appliance may be stopped automatically or manually.

The handpiece may be arranged to vibrate while it is in use, optionally or necessarily.

The appliance may operate on batteries, or by means of an electrical charger, or indeed it may be connected by an electric cable directly to mains or to a low voltage power supply that is in turn connected to mains.

Heat or Energy Modules

The handpiece includes a heat or energy module arranged to subject the applicator to a stimulus selected from: applying heat, low temperature, electricity, ultrasound energy, a magnetic field, or electromagnetic radiation.

The handpiece may include a plurality of modules from the above list. The handpiece may include a rotary module or a module for delivering vibration. These various modules may operate simultaneously, where appropriate. By way of example, it may be appropriate to apply jointly both heat and vibration, heat and light, light and vibration, ultrasound energy and light.

The handpiece may include a heater module, and it may be configured to heat the applicator to a predefined temperature as a function of the information read, e.g. a temperature lying in the range 35° C. to 45° C. When a handpiece includes a heater module, the heated surface of the handpiece in heating mode may reach a temperature that is 10° C. to 35° C. higher than ambient temperature, and preferably 15° C. to 25° C. higher in heating mode. The power delivered by the heater module may lie in the range 0.25 watts (W) to 10 W, and preferably lies in the range 0.5 W to 5 W.

A Peltier effect component may be used, where appropriate, in order to raise or lower temperature.

The handpiece may be associated with a plurality of applicators having encoders that correspond to respective different operating temperatures. For example, one of the applicators may correspond to operation without heating, i.e. at ambient temperature, and another applicator may trigger operation of the heater module.

In another example, the handpiece is associated with at least two applicators, having encoders each corresponding to heater operation but with two respective different temperature curves.

Composition

The composition may be a skincare, cleaning, or makeup composition and it may be presented in any suitable form. The composition may be solid. When the composition is solid, the surface that is used for application may be defined by a solid block of the composition, e.g. in the form of a stick or a pellet. The composition may be a makeup composition.

When solid, the composition may be cast or compacted, without reinforcement, or the applicator may include reinforcement, or the composition may be coated onto a substrate. The presence of reinforcement or of a substrate may make it possible to use a composition of smaller hardness or that presents lower cohesion.

The term "solid" should be understood as retaining its shape at 25° C., and not flowing under the effect of gravity.

When the composition is fluid, it may impregnate an applicator element of the applicator.

The applicator element may be pre-impregnated or it may be impregnated extemporaneously. The composition may also be applied extemporaneously on keratinous materials, and then the applicator element may come into contact with the composition once it has already been deposited on the materials for treatment.

Where appropriate, the applicator element and/or the composition may be moistened with water or with some other suitable solvent prior to being applied to keratinous materials.

With a composition that is solid or semi-solid, the handpiece may for example subject the applicator to a higher or lower temperature, adapted to the composition, so as to bring it to an optimum utilization temperature.

By way of example, the composition may soften as a function of a temperature rise and knowledge of the optimum temperature in terms of transfer onto human keratinous materials may be useful for achieving satisfactory application.

The applicator may include an item of information provided by the encoder that informs the handpiece about the temperature at which the composition should be raised in order to achieve such optimum application.

When fluid, the composition may present a variety of formulations or of forms.

It may be in the form of an aqueous, water-and-alcohol, or oily solution, a solution or a dispersion of the lotion or serum type, an emulsion of liquid or semi-liquid consistency of the milk type, obtained by dispersing an oily phase in an aqueous phase (O/W) or vice versa (W/O), or suspensions or emulsions of soft, or semi-solid consistency of the cream, aqueous gel, or anhydrous gel type, microemulsions, microcapsules, microparticles, or vesicular dispersions of the ionic and/or non-ionic type.

The aqueous phase contains water and possibly also an ingredient that is miscible in any concentration in water such as $C_1$ to $C_8$ lower alcohols such as ethanol, isopropanol, polyols such as propylene glycol, glycerol, sorbitol, or acetone, or ether.

The emulsion and coemulsion agents used in order to obtain a composition in the form of an emulsion are those generally used in the field of cosmetics. The emulsion may also contain lipid vesicles, and in particular liposomes.

The composition may optionally be pigmented.

The composition may in particular constitute a cleaning cream, a protective cream, a care product or treatment cream, a lotion, a gel, or a foam for skin care, such as a cleaning or disinfecting lotion, or a deodorant composition.

For application to the hair, the composition may be in the form of a lotion, serum, milk, O/W or W/O cream, gel, ointment, pomade, powder, or foam for use as a shampoo or as a conditioner, a liquid soap for cleaning the scalp, a composition for shaping the hair (setting, styling the hair), a cream, or a foaming gel for cleaning the hair.

The composition may contain at least one fat.

Fats suitable for use in the invention include mineral oils such as, for example, hydrogenated polyisobutene and vaseline oil, vegetable oils such as, for example, a liquid fraction of shea butter, sunflower oil, almond oil, apricot oil, animal oils such as, for example, perhydrosqualene, synthetic oils, in particular Purcellin oil, isorpropyl myristate, and ethyl hexyl palmitate, unsaturated fatty acids and fluorinated oils such as, for example, perfluoropolyethers. It is also possible to use fatty alcohols, fatty acids such as, for example, stearic acid, and for example, waxes, in particular silicone waxes, beeswax, candellila wax, rice wax, carnauba wax, paraffin wax, or polyethylene wax.

It is also possible to use silicone compounds such as silicone oils, and for example cyclomethicone and dimethicone, silicone waxes, resins, and gums.

As emulsifiers usable in the invention, mention may be made for example of glycerol stearate or laurate, sorbitol stearates or oleates, alkyl dimethiconecopolyols (with alkyl ≥8) and mixtures thereof for a W/O emulsion. It is also possible to use polyethylene glycol monostearate or monolaurate, polyoxyethylene sorbitol stearate or oleate, dimethiconecopolyols, and mixtures thereof for an O/W emulsion.

As solvents usable in the invention, mention may be made of alcohols such as ethanol, isopropanol, propylene glycol, and certain light cosmetic oils.

The composition may also contain sea water, spa water, and/or mineral water, in particular selected from vittel water, water from the Vichy basin, and Roche Posay water.

As hydrophilic gelling agents, mention may be made of carboxylic polymers such as carbomer, acrylic copolymers such as acrylate and alkylacrylate copolymers, polyacrylamides, polysaccharides such as cellulose derivatives such as hydroxyalkyl celluloses and in particular hydroxypropyl cellulose and hydroxyethyl cellulose, natural gums such as guar, carob, and xanthan gums, and clays.

As lipophilic gelling agents, mention may be made of modified clays such as bentones, metallic salts of fatty acids such as aluminum stearates and hydrophobic silica, or indeed ethyl cellulose and polyethylene, and mixtures thereof.

The composition may also include other ingredients commonly used in the fields concerned, selected from solvents, thickeners or gelling agents in aqueous or oily phase, coloring materials that are soluble in the medium of the composition, solid particles of the filler or pigment type, antioxidants, preservatives, fragrances, electrolytes, neutralizing agents, ultraviolet (UV) blocking agents such as sun filters, film-forming polymers, cosmetically-active agents having action that is beneficial for the skin or for keratinous fibers. Depending on their nature, these additives may be introduced in the fatty phase, in the aqueous phase, and/or in lipidic vesicles, and in particular in liposomes.

The composition may include an encapsulated compound that is released by applying energy, e.g. heat, and the handpiece may heat the applicator to a predefined temperature for this purpose.

Active Agents

The composition may contain at least one active agent. By way of example, the active agent(s) may be selected from agents suitable for acting on keratinous materials, such as agents that are cosmetologically and/or dermatologically active.

Amongst all of the agents that are usable in the present invention, particular mention may be made of α- or β-hydroxy acids, such as lactic acid, glycolic acid, citric and other fruit acids, 5-octanosylsalicylic acid, α-hydroxydecanoic acid, α-hydroxylauric acid, tartaric acid, glucuronic acid, galacturonic acid, acrylic acid, α-hydroxybutyric acid, α-hydroxyisobutyric acid, malic acid, mandelic acid, phosphoric acid, pyruvic acid, lactobionic acid, and salicylic acid and derivatives thereof such as n-octanoyl-5 salicylic acid, esters of hydroxy acids.

As examples of other active agents usable in the context of the present invention, mention may also be made of cosmetic oils, such as silicone oils, vegetable oils of the triglyceride type, hydrocarbon oils such as Parleam oil, and esters of fatty acids and of fatty alcohol, serving to impart emollient properties to the treatment.

The composition of the invention may contain:
  a cleaning or makeup-removing agent, in particular a makeup-removing oil, a surfactant, a peeling agent;
  an anti-aging agent, in particular a depigmenting agent, an anti-wrinkle active agent, an antioxidant, a liporestructuring agent, an agent enhancing skin microcirculation, an agent for combating whitening or graying of the hair;
  an agent for combating oily skins and/or oily hair;
  a self-tanning agent;
  a moistening or humectant agent;
  an agent for the area around the eyes;
  a thinning agent; or
  a sunscreen.

Cleaning or Makeup-Removing Agent

The cleaning or makeup-removing agent may be a makeup-removing oil.

Makeup-Removing Oil

Makeup-removing oils may be selected in particular from branched hydrocarbons, esters of fatty acid, and mixtures thereof.

The fatty acid esters are preferably selected from esters obtained from an alcohol having a linear or branched chain having 1 to 17 carbon atoms and a fatty acid having a linear or branched chain having 3 to 18 and preferably 12 to 17 carbon atoms.

As fatty acid esters usable as makeup-removing oils, mention may be made more particularly of ethyl hexyl palmitate, ethyl hexyl stearate, isopropyl myristate, isopropyl palmitate, isobutyl palmitate, pentaerythritol caprate/caprylate, cetearyl isononanoate, isodecyl isononanoate, isononyl isononanoate, isotridecyl isononanoate, and ethyl-2-hexyl caprate/caprylate.

The composition may contain at least one oil selected from branched hydrocarbons of mineral or synthetic origin such as, in particular: isoparaffin, isohexadecane, isododecane, hydrogenated polyisobutene, such as Parleam® oil.

It may also be advantageous for the composition to contain a short-chain ester such as dicaprylyl carbonate or a short-chain ether such as dicaprylyl ether, in order to improve the effectiveness of makeup remover.

The cleaning agent may in particular be a peeling agent.

Peeling Agent

The term "peeling agent" is used to mean any compound capable of acting:
  either directly on peeling by encouraging exfoliation, such as β-hydroxyacids (BHA), in particular salicylic acid and derivatives thereof (including n-octanoyl 5-salicylic acid otherwise known as capryloyl salicylic acid (INCI name)); α-hydroxyacids (AHA), such as glycolic, citric, lactic, tartric, malic, or mandelic acids; 8-hexadecene-1,16-dicarboxylic acid or 9-octadecene dioic acid; urea and derivatives thereof; gentisic acid and derivatives thereof; oligofucoses; cinnamic acid; extract of *Saphora japonica*; resveratrol and certain derivatives of jasmonic acid;
  or else on the enzymes involved in peeling or degrading corneodesmosomes, glycosidases, stratum corneum chymotryptic enzyme (SCCE), or other proteases (trypsine, chymotrypsine-like). Mention may be made of aminosulfonic compounds, and in particular 4-(2-hydroxyethyl)piperazine-1-propanesulfonic acid (HEPES); 2-oxothiazolidine-4-carboxylic acid (procysteine) and derivatives thereof; the derivatives of alpha-amino acids of the glycine type (as described in EP-0 852 949, and also sodium methyl glycine diacetate sold by BASF under the trade name Trilon M); honey; derivatives of sugar such as O-octanoyl-6-D-maltose and N-acetyl glucosamine.

The peeling agent may in particular be selected from: α-hydroxy acids such as citric, lactic, glycolic, malic, tartric, or mandelic acid; β-hydroxy acids such as salicylic acid and derivatives thereof, in particular n-octanoyl-5-salicylic acid; urea and derivatives thereof such as hydroxyethyl urea; aminosulfonic compounds and in particular (N-2 hydroxyethylpiperazine-N2-ethane) sulfonic acid (HEPES); sugar derivatives and in particular O-octanoyl-6-D-maltose and honey; 8-hexadecene-1,16-dicarboxylic acid; derivatives of 2-oxothiazolidine-4-carboxylic acid (procysteine); an extract of *Saphora japonica*; resveratrol; cinnamic acid; and jasmonic acid and derivatives thereof such as (1R,2R)3-hydroxy-2-pentyl-cyclopentane-acetic acid.

As preferred peeling agents, it is possible to use α-hydroxy acids such as citric, lactic, glycolic, malic, tartric, or mandelic acid; β-hydroxy acids such as salicylic acid and derivatives thereof, in particular n-octanoyl-5-salicylic acid; urea and derivatives thereof such as hydroxyethyl urea; aminosulfonic compounds and in particular (N-2 hydroxyethylpiperazine-N2-ethane) sulfonic acid (HEPES); derivatives of 2-oxothiazolidine-4-carboxylic acid (procysteine); an extract of *Saphora japonica*.

The peeling agent may represent 0.1% to 10%, and preferably 0.1% to 5%, and more preferably 0.1% to 2%, better 0.5% to 0.6% of the total weight of the peeling composition.

The composition may include an anti-age agent, which may be a depigmenting agent.

As other peeling agents suitable for use in the composition of the invention, mention be made of:
oligofructoses, EDTA and derivatives thereof, laminaria extracts, O-linoleyl-6-D-gluocose; (3-hydroxy-2-pentylcyclopentyl) acetic acid, glycerol trilactate, O-octanyl-6'-D-maltose, S carboxymethyl cysteine, silica-containing derivatives of salicylate such as those described in patent EP 0 796 861, oligofucases such as those described in patent EP 0 218 200, salts of 5-acyl salicylic acid, agents having effects on transglutaminase as in patent EP 0 899 330;
extract of the flower *ficus opuntia indica* such as Exfolactive® from Silab;
8-hexadecene 1,16-dicarboxylic acid;
esters of glucose and of vitamin F; and
mixtures thereof.

As preferred peeling agents, mention may be of beta-hydroxyacids, such as n-octanoyl 5-salicylic acid; urea; glycolic, citric, lactic, tartric, malic, or mandelic acids; 4-(2-hydroxyethyl)piperazine-1-propanesulfonic acid (HEPES); extract of *Saphora japonica*; honey; N-acetyl glucosamine; sodium methyl glycine diacetate; and mixtures thereof.

Still more preferably, compositions of the invention make use of a peeling agent selected from n-octanoyl 5-salicylic acid; urea; 4-(2-hydroxyethyl)piperazine-1-propanesulfonic acid (HEPES); extract of *Saphora japonica*; honey; N-acetyl glucosamine; sodium methyl glycine diacetate; and mixtures thereof.

The cleaning or peeling agent may contain a surfactant, which may advantageously serve to generate foam.

Surfactant

Non-Ionic Foaming Surfactant

The composition may contain one or more non-ionic foaming surfactants. These surfactants are foaming surfactants suitable for cleaning keratinous materials.

Foaming surfactants are detergents that differ from emulsifiers in their hydrophilic lipophilic balance (HLB) value, where HLB is the ratio between the hydrophilic portion and the lipophilic portion in the molecule. The term HLB is well known to the person skilled in the art and is described for example in "The HLB system, a time-saving guide to emulsifier selection" (published by ICI Americas Inc., 1984). For emulsifiers, HLB generally lies in the range 3 to 8 for preparing W/0 emulsions and in the range 8 to 18 for preparing O/W emulsions, where as foaming surfactants generally have HLB greater than 20.

The non-ionic foaming surfactants for the composition of the invention may be selected in particular from alkyl polyglucosides (APG), esters of glycerol oxyalkylenes, esters of sugar oxyalkylenes, and mixtures thereof. They are preferably APGs.

As alkylpolyglucosides, it is preferable to use those that contain an alkyl group having 6 to 30 carbon atoms and preferably 8 to 16 carbon atoms, and containing a glucoside group preferably comprising 1.2 to 3 glucoside units. The alkylpolyglucosides may be selected for example from decylglucoside (Alkyl-C9/C11-polyglucoside (1.4)) as the product sold under the name Mydol 10® by the supplier Kao Chemicals or the product sold under the name Plantacare 2000 UP® by the supplier Cognis; caprylyl/capryl glucoside such as the product sold under the name Plantacare KE 3711® by the supplier Cognis; laurylglucoside such as the product sold under the name Plantacare 1200 UP® by the supplier Cognis; cocoglucoside such as the product under the name Plantacare 818 UP® by the supplier Cognis; caprylylglucoside such as the product sold under the name Plantacare 810 UP® by the supplier Cognis; and mixtures thereof.

Alkoxylated glycerol esters are in particular polyethyloxylated derivatives of glyceryl and fatty acid esters and hydrogenated derivatives thereof. These alkoxylated glycerol esters may be selected, for example, from hydrogenated and ethyloxylated fatty acids and glyceryl esters such as PEG-200 hydrogenerated glyceryl palmate sold under the name Rewoderm LI-S 80 by the supplier Goldschmidt; ethyloxylated glyceryl cocoates such as PEG-7 glyceryl cocoate sold under the name Tegosoft GC by the supplier Goldschmidt; and PEG-30 glyceryl cocoate sold under the name Rewoderm LI-63 by the supplier Goldschmidt; and mixtures thereof.

Esters of alkoxylated sugars are in particular polyethylene glycol ethers, fatty acid esters, and sugar. These alkoxylated sugar esters may be selected for example from ethyloxylated glucose esters such as PEG-120 methyl glucose dioleate sold under the name Glucamate DOE 120 by the supplier Amerchol.

The non-ionic surfactant may be an alkylpolyglucoside which may be selected in particular from decylglucoside, caprylyl/capryl glucoside, laurylglucoside, cocoglucoside, caprylylglucoside, and mixtures thereof.

The composition may contain a quantity of non-ionic foaming surfactant(s) (as active material) that may for example lie in the range 1% to 50% by weight, e.g. in the range 1% to 40% by weight, or 2% to 30% by weight, relative to the total weight of the composition.

In addition to the non-ionic foaming surfactant, the composition may contain one or more foaming surfactants selected from surfactants that are anionic, amphoteric, and zwitterionic.

Anionic Surfactants

Anionic foaming surfactants that may be added to the composition of the invention may in particular be selected from anionic derivatives of proteins of plant origin or of silk proteins, phosphates and alkylphosphates, carboxylates, sulfosuccinates, amino acid derivatives, alkyl sulfates, alkyl ether sulfates, sulfonates, isethionates, taurates, alkyl sulfoacetates, polypeptides, anionic alkyl polyglucoside derivatives, and mixtures thereof.

Anionic derivatives of proteins of plant origin are protein hydrolysates with a hydrophobic group, said hydrophobic group possibly being naturally present in the protein or being added by reaction of the protein and/or protein hydrolysate with a hydrophobic compound. The proteins are of plant origin or are derived from silk, and the hydrophobic group may in particular be a fatty chain, for example an alkyl chain containing 10 to 22 carbon atoms. More particular examples of anionic derivatives of proteins of plant origin that may be mentioned are hydrolysates of apple, wheat, soybean, oat proteins comprising an alkyl chain containing 10 to 22 carbon atoms, and their salts. The alkyl chain may in particular be a lauryl chain and the salt may be a sodium, potassium, and/or ammonium salt.

Examples of protein hydrolysates with a hydrophobic group that may be mentioned are salts of silk protein hydrolysates modified by lauric acid such as the product sold under the name KAWA SILK by the supplier Kawaken; wheat protein hydrolysate salts modified with lauric acid, such as the potassium salt sold under the name Aminofoam W OR by the supplier Croda (CTFA name: Potassium Lauroyl Wheat Amino Acids) and the sodium salt sold under the name PROTEOL LW 30 by the supplier Seppic (CTFA name: Sodium Lauroyl Wheat Amino Acids); oat protein hydrolysate salts comprising an alkyl chain containing 10 to 22 carbon atoms, and more especially oat protein hydrolysate salts modified with lauric acid, such as the sodium salt sold under the name PROTEOL OAT (30% aqueous solution) by the supplier Seppic (CTFA name: Sodium Lauroyl oat amino acids); apple protein hydrolysate salts comprising an alkyl chain containing 10 to 22 carbon atoms, such as the sodium salt sold under the name PROTEOL APL (30% hydroglycolic solution) by the supplier Seppic (CTFA name: Sodium Cocoyl Apple Amino Acids). It is also possible to mention the mixture of lauroyl amino acids (aspartic, glutamic, glycine, alanine) neutralized with sodium N-methylglycinate, sold under the name PROTEOL SAV 50 S by the supplier Seppic (CTFA name: Sodium Cocoyl Amino Acids).

Phosphates and alkylphosphates that may be mentioned, for example, are monoalkyl phosphates and dialkyl phosphates, such as lauryl monophosphate sold under the name MAP 20® by the supplier Kao Chemicals, the potassium salt of dodecyl-phosphoric acid, the mono- and di-ester mixture (mainly diester) sold under the name CRAFOL AP-31® by the supplier Cognis, the monoester and di-ester mixture of octylphosphoric acid, sold under the name CRAFOL AP-20® by the supplier Cognis, the monoester and diester mixture of ethoxylated 2-butyloctanol phosphoric acid (7 moles of EO), sold under the name ISOFOL 12 7 EO-PHOSPHATE ESTER® by the supplier Condea, the potassium or triethanolamine salt of mono-alkyl (C12-C13) phosphate sold under the references ARLATONE MAP 230K-40® and ARLATONE MAP 230T-60® by the supplier Uniqema, potassium lauryl phosphate sold under the name DERMALCARE MAP XC-99/09® by the supplier Rhodia Chimie, and potassium cetyl phosphate sold under the name ARLATONE MAP 160K by the supplier Uniqema.

Examples of carboxylates that may be mentioned are:
Amido ethercarboxylates (AEC), such as sodium lauryl amido ether carboxylate (3 EO), sold under the name AKYPO FOAM 30® by the supplier Kao Chemicals;
polyethyloxylated carboxylic acid salts, such as ethyloxylated (6 EO) sodium lauryl ether carboxylate (C12-14-16 65/25/10) sold under the name AKYPO SOFT 45 NV® by the supplier Kao Chemicals, polyethyloxylated and carboxymethylated fatty acids from olive oil sold under the name OLIVEM 400® by the supplier BIOLOGIA E TECNOLOGIA, ethyloxylated (6 EO) sodium tridecyl ether carboxylate sold under the name NIKKOL ECTD-6NEX® by the supplier Nikkol;
fatty acid salts (soaps) having a C6 to C22 alkyl chain, neutralized with an organic or mineral base such as potassium hydroxide, sodium hydroxide, triethanolamine, N-methyl glucamine, lysine, or arginine.

Examples of amino acid derivatives that may in particular be mentioned are alkali amino acid salts, such as:
sarcosinates, such as sodium lauroyl sarcosinate sold under the name SARKOSYL NL 97® by the supplier Ciba or sold under the name ORAMIX L 30® by the supplier Seppic, sodium myristoyl sarcosinate sold under the name NIKKOL SARCOSINATE MN® by the supplier Nikkol, sodium palmitoyl sarcosinate sold under the name NIKKOL SARCOSINATE PN® by the supplier Nikkol;
alaninates, such as sodium N-lauroyl-N methyl amidopropionate sold under the name SODIUM NIKKOL ALANINATE LN 30® by the supplier Nikkol, or sold under the name ALANONE ALE® by the supplier Kawaken, N-lauroyl N-methyl alanine triethanolamine sold under the name ALANONE ALTA® by the supplier Kawaken;
glutamates, such as triethanolamine mono-cocoyl glutamate sold under the name ACYLGLUTAMATE CT-12® by the supplier Ajinomoto, triethanolamine lauroyl glutamate sold under the name ACYLGLUTAMATE LT-12® by the supplier Ajinomoto;
aspartates, such as the mixture of triethanolamine N-lauroyl aspartate/triethanolamine N-myristoyl aspartate sold under the name ASPARACK® by the supplier Mitsubishi;
glycine derivatives (glycinates), such as sodium N-cocoyl glycinate sold under the names AMILITE GCS-12® and AMILITE GCK 12 by the supplier Ajinomoto;
citrates, such as the citric mono-ester of ethyloxylated coco alcohols (9 moles), sold under the name WITCONOL EC 1129 by the supplier Goldschmidt;
galacturonates, such as sodium dodecyl d-galactoside uronate sold by the supplier Soliance.

Examples of sulfosuccinates that may be mentioned, for example, are ethyloxylated (3 EO) lauryl alcohol (C12/C14 70/30) mono-sulfosuccinate sold under the names SETACIN 103 SPECIAL®, REWOPOL SB-FA 30 K 4® by the supplier Witco, the disodium salt of a hemi-sulfosuccinate of C12-C14 alcohols, sold under the name SETACIN F SPECIAL PASTE® by the supplier Zschimmer Schwarz, the ethyloxylated (2 EO) disodium oleamidosulfosuccinate sold under the name STANDAPOL SH 135® by the supplier Cognis, the ethyloxylated (5 EO) lauric amide mono-sulfosuccinate sold under the name LEBON A-5000® by the supplier Sanyo, the ethyloxylated (10 EO) disodium salt of lauryl citrate mono-sulfosuccinate sold under the name REWOPOL SB CS 50® by the supplier Witco, the ricinoleic mono-ethanolamide of mono-sulfosuccinate sold under the name REWODERM S1333® by the supplier Witco. It is also possible to use polydimethylsiloxane sulfosuccinates such as disodium dimethicone PEG-12 sulfosuccinate sold under the name MACKANATE-DC30 by the supplier Mac Intyre.

Examples of alkyl sulfates that may be mentioned, for example, are triethanolamine lauryl sulfate (CTFA name: TEA Lauryl Sulfate) such as the product sold by the supplier Huntsman under the name EMPICOL TL40 FL or that sold by the supplier Cognis under the name TEXAPON T42, the compositions being in 40% aqueous solution. It is also possible to mention ammonium lauryl sulfate (CFTA name: Ammonium Lauryl Sulfate) such as the product in 30% aqueous solution sold by the supplier Huntsman under the name EMPICOL AL 30FL.

Examples of alkyl ether sulfates that may be mentioned are sodium lauryl ether sulfate (CTFA name: Sodium Laureth Sulfate) such as those sold under the names TEXAPON N40 and TEXAPON AOS 225 UP by the supplier Cognis, ammonium lauryl ether sulfate (CTFA name: Ammonium Laureth Sulfate) such as that sold under the name STANDAPOL EA-2 by the supplier Cognis.

Examples of sulfonates that may be mentioned are alpha-olefin sulfonates such as sodium (C14-16) alpha-olefin sulfonate sold under the name BIO-TERGE AS-40® by the supplier Stepan, sold under the names WITCONATE AOS PROTEGE® and SULFRAMINE AOS PH 12® by the supplier Witco or sold under the name BIO-TERGE AS-40 CG® by the supplier Stepan, the secondary sodium olefin sulfonate sold under the name HOSTAPUR SAS 30® by the supplier Clariant; straight chain alkyl aryl sulfonates such as sodium xylene sulfonate sold under the names MANROSOL SXS30®, MANROSOL SXS40®, MANROSOL SXS93® by the supplier Manro.

Examples of isethionates that may be mentioned are acyl-isethionates such as sodium cocoyl-isethionate, for example the product sold under the name JORDAPON CI P® by the supplier Jordan.

Examples of taurates that may be mentioned are the sodium salt of palm kernel oil methyltaurate sold under the name HOSTAPON CT PATE® by the supplier Clariant; N-acyl N-methyltaurates such as sodium N-cocoyl N-methyltaurate sold under the name HOSTAPON LT-SF® by the supplier Clariant or sold under the name NIKKOL CMT-30-T® by the supplier Nikkol, sodium palmitoyl methyltaurate sold under the name NIKKOL PMT® by the supplier Nikkol.

In particular, the anionic derivatives of alkyl-polyglucosides may be citrates, tartrates, sulfosuccinates, carbonates and ethers of glycerol obtained from alkyl polyglucosides. Examples that may be mentioned are the sodium salt of the tartaric ester of cocoyl (1,4) polyglucoside, sold under the name EUCAROL AGE-ET® by the supplier Cesalpinia, the disodium salt of sulfosuccinic ester of cocoyl (1,4) polyglucoside, sold under the name ESSAI 512 MP® by the supplier Seppic, the sodium salt of the citric ester of cocoyl (1,4) polyglucoside sold under the name EUCAROL AGE-EC® by the supplier Cesalpinia.

Amphoteric and Zwitterionic Foaming Surfactants

The zwitterionic and amphoteric surfactants may, for example, be selected from betaines, N-alkylamidobetaines and their derivatives, sultaines, alkyl polyaminocarboxylates, alkylamphoacetates and mixtures thereof.

Examples of betaines that may in particular be mentioned are alkylbetaines such as cocobetaine, for example, such as the product sold under the name DEHYTON AB-30® by the supplier Cognis, laurylbetaine such as the product sold under the name GENAGEN KB® by the supplier Clariant, ethyloxylated (10 EO) laurylbetaine, such as the product sold under the name LAURYLETHER (10 EO) BETAINE® by the supplier Shin Nihon Rica, ethyloxylated (10 EO) stearylbetaine such as the product sold under the name STEARYLETHER (10 EO) BETAINE® by the supplier Shin Nihon Rica.

Examples of N-alkylamidobetaines and their derivatives that may be mentioned are cocamidopropyl betaine sold under the name LEBON 2000 HG® by the supplier Sanyo, or sold under the name EMPIGEN Be by the supplier Albright & Wilson, lauramidopropyl betaine sold under the name REWOTERIC AMB12P® by the supplier Witco.

Examples of sultaines that may be mentioned are hydroxysultaines, for example cocamidopropyl hydroxysultaine, such as the product sold under the name REWOTERIC AM CAS by the supplier Golschmidt-Degussa, or the product sold under the name CROSULTAINE C-50® by the supplier Croda.

Examples of alkyl polyaminocarboxylates (APAC) that may be mentioned are sodium cocoylpolyaminocarboxylate sold under the name AMPHOLAK 7 CX/C®, and AMPHOLAK 7 CX® by the supplier Akzo Nobel, sodium stearyl polyamidocarboxylate sold under the name AMPHOLAK 7 TX/C by the supplier Akzo Nobel, sodium carboxymethyl oleylpolypropylamine, sold under the name AMPHOLAK XO7/C® by the supplier Akzo Nobel.

Examples of alkylamphoacetates that may be mentioned are N-disodium N-cocoyl-N-carboxymethoxyethyl-N-carboxymethyl ethylenediamine (CTFA name: disodium cocoamphodiacetate) such as the product sold under the name MIRANOL C2M CONCENTER NP® by the supplier Rhodia, N-sodium N-cocoyl-N-hydroxyethyl-N-carboxymethyl-ethylenediamine (CTFA name: sodium cocamphoacetate), and sodium cocoamphohydroxypropyl sulfonate sold under the name MIRANOL CSE by the supplier Rhodia.

The anionic, amphoteric and zwitterionic foaming surfactants, when present in the composition, may be in a quantity (of active substance) of, for example, from 0.5% to 15% by weight, preferably from 1% to 10% by weight relative to the total composition weight.

In addition to the non-ionic surfactant, the composition may contain, as the foaming surfactant, at least one anionic derivative of proteins of plant origin or from silk. The composition may contain at least one alkylpolyglucoside and at least one anionic derivative of proteins of plant origin or from silk.

Anti-Ageing Active Ingredients

The composition may include a depigmenting agent.

Depigmenting Agent

Depigmenting agents that may in particular be used are vitamin C and its derivatives, and in particular vit CG, CP and 3-O ethyl vitamin C, alpha and beta arbutin, ferulic acid, lucinol and its derivatives, kojic acid, resorcinol and its derivatives, tranexamic acid and its derivatives, gentisic acid, homogentisate, methyl gentisate or homogentisate, dioic acid, D calcium pantheteine sulfonate, lipoic acid, ellagic acid, vitamin B3, linoleic acid and its derivatives, ceramides and their homologs, derivatives from plants such as camomile, bearberry, the aloe family (vera, ferox, bardensis), mulberry, skullcap, a kiwi fruit extract (*Actinidia chinensis*) sold by the supplier Gattefosse, a *Paeonia suffructicosa* root extract such as that sold by the supplier Ichimaru Pharcos under the name Botanpi Liquid B®, and a brown sugar extract (*Saccharum officinarum*), such as the molasses extract sold by the supplier Taiyo Kagaku under the name Molasses Liquid; this list is not exhaustive.

Preferred depigmenting agents that may be used are vitamin C and its derivatives and in particular vit CG, CP and 3-O ethyl vitamin C, alpha and beta arbutin, ferulic acid, kojic acid, resorcinol and its derivatives, D calcium pantheteine sulfonate, lipoic acid, ellagic acid, vitamin B3, a kiwi fruit extract (*Actinidia chinensis*) sold by the supplier Gattefosse, a *Paeonia suffructicosa* root extract such as that sold by the supplier Ichimaru Pharcos under the name Botanpi Liquid B®.

The composition may include an anti-wrinkle active ingredient.

Anti-Wrinkle Active Ingredient

In the context of the present invention, the term "anti-wrinkle active ingredient" means a compound of natural or synthetic origin producing a biological effect, such as an increase in the synthesis and/or activity of certain enzymes, when it is brought into contact with a zone of wrinkled skin, that effect having the result of reducing the appearance of wrinkles and/or fine lines.

Examples of anti-wrinkle active ingredients that may be used in the present invention may be selected from: desquamating agents; anti-glycation agents; NO-synthase inhibitors; agents stimulating the synthesis of dermal or epidermal macromolecules and/or preventing their degradation; agents stimulating the proliferation of fibroblasts and/or keratinocytes; agents stimulating or reducing keratinocyte differentiation; myorelaxing and/or dermo-relaxing agents; free radical scavengers; and mixtures thereof.

Examples of such compounds are: adenosine and its derivatives; retinol and its derivatives such as retinyl palmitate; ascorbic acid and its derivatives such as ascorbyl magnesium phosphate and ascorbyl glucoside; tocopherol and its derivatives such as tocopheryl acetate; nicotinic acid and its precursors such as nicotinamide; ubiquinone; glutathione and its precursors such as L-2-oxothiazolidine-4-carboxylic acid; C-glycoside compounds and their derivatives, such as those described in particular in application EP-1 345 919, in particular C-beta-D-xylopyranoside-2-hydroxy-propane such as that described in particular in application EP-1 345 919; plant extracts, in particular criste marine extracts and olive leaf extracts, as well as plant proteins and their hydrolysates such as rice or soybean protein hydrolysates; extracts from algae, in particular from laminaria; bacterial extracts; sapogenins such as diosgenin and extracts from Dioscoreae, in particular from wild yam, containing them; α-hydroxyacids; β-hydroxyacids, such as salicylic acid or n-octanoyl-5-salicylic acid; oligopeptides and pseudodipeptides and their acyl derivatives, in particular {2-[acetyl-(3-trifluoromethyl-phenyl)-amino]-3-methyl-butyrylamino}acetic acid and lipopeptides sold by the supplier SEDERMA under the commercial names Matrixyl 500 and Matrixyl 3000; lycopene; manganese and magnesium salts, in particular gluconates; and mixtures thereof.

Examples of adenosine derivatives that may in particular be mentioned are non-phosphated adenosine derivatives such as: 2'-deoxyadenosine; 2',3'-isopropoylidene adenosine; toyocamycin; 1-methyladenosine; N-6-methyladenosine; adenosine N-oxide; 6-methylmercaptopurine riboside; or 6-chloropurine riboside.

Other adenosine derivatives comprise agonists of adenosine receptors including phenylisopropyl-adenosine ("PIA"), 1-methylisoguanosine, N6-cyclohexyladenosine (CHA), N6-cyclopentyladenosine (CPA), 2-chloro-N-6-cyclopentyladenosine, 2-chloroadenosine, N6-phenyladenosine, 2-phenylaminoadenosine, MECA, N6-phenethyladenosine, 2-p-(2-carboxy-ethyl) phenethyl-amino-5'-N-ethylcarboxamido-adenosine (CGS-21680), N-ethylcarboxamido-adenosine (NECA), 5' (N-cyclopropyl)-carboxamidoadenosine, DPMA (PD 129,944) and metrifudil.

Other adenosine derivatives include compounds that increase the intracellular concentration of adenosine, such as erythro-9-(2-hydroxy-3-nonyl) adenine ("EHNA") or iodotubercidine.

Still more adenosine derivatives include salts and alkyl esters.

The term "C-glycoside derivative" means the compounds described in application EP-1 345 919 with formula (I) below:

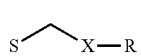

(I)

in which;
S represents a monosaccharide or a polysaccharide with up to 20 sugar units in the pyranose and/or furanose form, L and/or D series, said mono- or polysaccharide having at least one hydroxyl function that must be free and/or optionally one or more amine functions that may be protected;

The concatenation S—CH2-X represents a C-anomeric concatenation;

X represents a group selected from: —CO—, —CH(OH)—, —CH(NR1R2)-, —CHR'—, —C(=CHR')—;

R represents a linear or branched, saturated or unsaturated alkyl, perfluoroalkyl, hydrofluoroalkyl chain, a cycloalkyl, cycloperfluoroalkyl, cyclohydrofluoroalkyl cycle comprising 1 to 18 carbon atoms, or a phenyl or benzyl radical, said chain, said cycle or said radical possibly being interrupted by one or more heteroatoms selected from oxygen, sulfur, nitrogen, silicon, and optionally substituted with at least one radical selected from —OR'1, —SR"1, —NR"'1R'2, —COOR"2, —CONHR"'2, —CN, halogen, perfluoroalkyl, hydrofluoroalkyl and/or at least one cycloalkyl, aryl, heterocyclic radical, optionally substituted;

R', R1, R2, which may be identical or different, have the definition given for R and may also represent a hydrogen and a hydroxyl radical;

R'1, R'2, R"1, R"2, R"'1, R"'2, which may be identical or different, represent a hydrogen atom, or a radical selected from a linear or branched, saturated or unsaturated alkyl, hydroxyl, perfluoroalkyle and/or hydrofluoroalkyl radical containing 1 to 30 carbon atoms.

The composition may include an antioxidant.

Antioxidants

Tocopherol and its esters may be mentioned in particular, especially tocopherol acetate; ascorbic acid and its derivatives, in particular magnesium ascorbyl phosphate and ascorbyl glucoside; ferulic acid; serine; ellagic acid, phloretin, polyphenols, tannins, tannic acid, epigallocathechins and natural extracts containing them, anthocyans, rosemary extracts, olive leaf extracts such as those from the supplier Silab, green tea extracts, resveratrol and its derivatives, ergothineine, N acetylcysteine, an extract from the brown algae *pelvetia canaliculata* such as Pelvetiane® from the supplier Secma, chlorogenic acid, biotin, chelating agents, such as BHT, BHA, N,N'-bis(3,4,5-trimethoxybenzyl)ethylenediamine and its salts; idebenone, plant extracts such as Pronalen Bioprotect™ from the supplier Provital; Q10 co enzyme, bioflavonoids, SODs, phytantriol, lignans, melatonin, pidolates, gluthatione, caprylyl glycol, phloretin, Totarol™ or *Podocarpus totara* extract containing totarol (totara-8,11,13-trienol or 4b,5,6,7,8,8a,9,10-octahydro-4-b, 8,8-trimethyl-1 (1-methylethyl)-phenanthren-2-ol; a jasmin extract such as that sold by the supplier SILAB under the name Helisun0; hesperitin laurate such as Flavagrum PEG® from the supplier Engelhard Lyon; a *Paeonia suffructicosa* root extract such as that sold by the supplier Ichimaru Pharcos under the name Botanpi Liquid B®; a lychee extract such as the lychee pericarp extract sold by the supplier Cognis under the name Litchiderm LS 9704©, a pomegranate fruit extract (*Punica Granatum*), such as that sold by the supplier Draco Natural products.

Other anti-ageing agents that may be mentioned are DHEA and its derivatives, boswellic acid, rosemary extracts, carotenoids (B carotene, zeaxanthin, lutein), cysteic acid, copper derivatives, and jasmonic acid.

Preferred antioxidants that may in particular be used are ferulic acid; serine; phloretin, a pomegranate extract, biotin, chelating agents such as BHT, BHA, N,N'-bis(3,4,5-trimethoxybenzyl)ethylenediamine and its salts, caprylyl glycol, phloretin, Totarol™, a jasmin extract such as that sold par SILAB under the name Helisun®; hesperitin laurate such as Flavagrum PEG® from the supplier Engelhard Lyon; and a *Paeonia suffructicosa* root extract such as that sold by the supplier Ichimaru Pharcos under the name Botanpi Liquid B®.

The composition may include a liporestructuring agent.

Liporestructuring Agents

The term "liporestructuring agents" as used in the context of the invention means agents that are capable of stimulating lipogenesis and encouraging adipocytary differentiation, thereby avoiding or slowing the loss of fats contained in the tissues supporting the skin, also termed "loss of skin lipo-structure".

The term "skin lipo-structure" means the network of fat cells that form volumes on which facial skin sits and is molded.

These agents may be intended to:
reduce the loss of skin density and/or the loss of the skin lipo-structure, in particular on the cheeks and the area around the eyes; and/or
prevent collapse and/or hollowing of the volumes of the face, the loss of skin consistency and/or its support, in particular on the cheeks and the area around the eyes; and/or
improve the volumes underlying the skin of the face and/or neck, in particular on the cheeks, the oval of the face and the area around the eyes; and/or
improve the density, elasticity and support of the skin, in particular on the cheeks, the oval of the face and the area around the eyes; and/or
remodel the facial features, in particular the oval of the face.

Examples of liporestructuring agents that may in particular be mentioned are a black tea extract such as the fermented black tea extract sold by the supplier Sederma under the name Kombuchka®, and an *Artemisia abrotanum* extract, such as that sold by the supplier Silab under the name Pulpactyl®.

The composition may include an agent encouraging skin microcirculation.

Agent Encouraging Skin Microcirculation

The active ingredient acting on skin microcirculation may be used to avoid fading of the complexion and/or to improve the appearance of the area around the eyes, in particular to reduce dark rings. It may, for example, be selected from an extract of maritime pine bark such as Pycnogenol® from the supplier Biolandes, manganese gluconate (Givobio GMn® from the supplier Seppic), an *Ammi visnaga* extract such as Visnadine from the supplier Indena, lupin extract (Eclaline® from the supplier Silab), hydrolyzed wheat protein/palmitic acid coupled with palmitic acid such as Epaline 100 from the supplier Laboratoires carilène, Seville orange flower extract (Remoduline® from the supplier Silab), vitamin P and its derivatives such as sodium methyl-4 esculetol mono-ethanoate sold under the name Permethol® by the supplier Sephytal, extracts from ruscus, from horse chestnut, from ivy, ginseng and melilot, caffeine, nicotinate and its derivatives, lysine and its derivatives such as Asparlyne® from the supplier Solabia, a black tea extract such as Kombuchka from the supplier Sederma; rutine salts: a *corallina officinalis* algae extract such as that sold from the supplier CODIF; and mixtures thereof.

Preferred agents encouraging skin microcirculation that may be mentioned are caffeine, a Seville orange flower extract, a black tea extract, rutine salts, and a *corallina officinalis* salt extract.

The composition may include an active ingredient for combating greasy skin and/or greasy hair.

Active Ingredient for Combating Greasy Skin and/or Greasy Hair

The active ingredient for combating greasy skin may be a seboregulator or an anti-seborrheic agent.

The term "seboregulator or anti-seborrheic agent" means agents that are capable of regulating the activity of the sebaceous glands.

Particular examples that may be mentioned are:
retinoic acid, benzoyl peroxide, sulfur, vitamin B6 (or pyridoxine), selenium chloride, criste marine;
a mixture of cinnamon, tea and octanoylglycine extracts such as Sepicontrol A5 TEA® from the supplier Seppic;
a mixture of cinnamon, sarcosine and octanoylglycine sold in particular by the supplier SEPPIC under the name Sepicontrol A5®;
zinc salts such as zinc gluconate, zinc pyrrolidone carboxylate (or zinc pidolate), zinc lactate, zinc aspartate, zinc carboxylate, zinc salicylate, zinc cysteate;
copper derivatives and in particular copper pidolate such as Cuivridone® from the supplier Solabia;
plant extracts from the species *Arnica montana*, *Cinchona succirubra*, *Eugenia caryophyllata*, *Humulus lupulus*, *Hypericum perforatum*, *Mentha piperita*, *Rosmarinus officinalis*, *Salvia oficinalis* and *Thymus vulgaris*, all sold for example by the supplier MARUZEN;
meadowsweet extracts (*spiraea ulamaria*) such as that sold under the name Sebonormine® by the supplier Silab;
*laminaria saccharina* algae extracts such as that sold under the name Phlorogine® by the supplier Biotechmarine;
mixtures of extracts from pimpernel roots (*sanguisorba officinalis/poterium officinale*), ginger rhizomes (*zingiber officinalis*) and cinnamon bark (*cinnamomum cassia*) such as that sold under the name Sebustop® by the supplier Solabia;
linseed extracts such as that sold under the name Linumine® by the supplier Lucas Meyer;
*Phellodendron* extracts such as that sold under the name *Phellodendron* extract BG by the supplier Maruzen or Oubaku liquid B by the supplier Ichimaru Pharcos;
mixtures of argan oil, *serenoa serrulata* (saw palmetto) extract and sesame seed extract such as that sold under the name Regu SEB® by the supplier Pentapharm;
mixtures of extracts of epilobe, of *terminalia chebula*, of capucine and of bioavailable zinc (microalgae) such as that sold under the name Seborilys® by the supplier green tech;
*Pygeum afrianum* extracts such as that sold under the name *Pygeum afrianum* sterolic lipid extract by the supplier Euromed;
*serenoa serrulata* extracts, such as that sold under the name Viapure Sabal by the supplier Actives International, or those sold by the supplier Euromed;
mixtures of extracts of plantain, *berberis aquifolium* and sodium salicylate, such as that sold under the name Seboclear® by the supplier Rahn;
clove extract, such as that sold under the name Clove extract Powder by the supplier Maruzen;
argan oil, such as that sold under the name Lipofructyl® from the supplier Laboratoires Serobiologiques;
lactic protein filtrates, such as that sold under the name Normaseb® by the supplier Sederma;
*laminaria* algae extracts such as that sold under the name Laminarghane® by the supplier Biotechmarine;

*laminaria digitata* algae oligosaccharides, such as that sold under the name Phycosaccharide AC by the supplier Codif;

sugar cane extracts, such as that sold under the name Policosanol® by the supplier Sabinsa;

sulfonated schist oil, such as that sold under the name Ichtyol Pale® by the supplier Ichthyol;

meadowsweet (*spiraea ulmaria*) extracts, such as that sold under the name Cytobiol® Meadowsweet by the supplier Libiol;

sebacic acid, especially that sold in the form of a sodium polyacrylate gel under the name Sebosoft® by the supplier Sederma;

glucomannans extracted from konjac tubers and modified with alkylsulfonate chains, such as that sold under the name Biopol Beta by the supplier Arch Chemical;

*Sophora angustifolia* extracts, such as that sold under the name Sophora powder or Sophora extract by the supplier Bioland;

*cinchona succirubra* bark extracts, such as that sold under the name Red bark HS by the supplier Alban Muller;

*quillaja saponaria* extracts, such as that sold under the name Panama wood HS by the supplier Alban Muller;

glycine grafted onto an undecylene chain, such as that sold under the name Lipacide UG OR by the supplier Seppic;

the mixture of oleanolic acid and nordihydroguaiaretic acid, such as that sold in the form of a gel under the name AC.Net by the supplier Sederma;

phthalimidoperoxyhexanoic acid;

trialkyl(C12-C13) citrate sold under the name COSMACOL® ECI by the supplier Sasol; trialkyl(C14-C15) citrate sold under the name COSMACOL® ECL by the supplier Sasol;

10-hydroxydecanoic acid, and especially mixtures of 10-hydroxydecanoic acid, sebacic acid and 1,10-decandiol such as that sold under the name Acnacidol® BG by the supplier Vincience; and mixtures thereof.

Preferred anti-seborrheic agent active ingredients that may be mentioned are:

benzoyl peroxide, vitamin B6 (or pyridoxine);

zinc salts such as zinc gluconate, zinc pyrrolidone carboxylate (or zinc pidolate), zinc lactate, zinc aspartate, zinc carboxylate, zinc salicylate, zinc cysteate;

extracts from meadowsweet (*spiraea ulamaria*), such as that sold under the name Sebonormine® by the supplier Silab;

*laminaria saccharina* algae extracts, such as that sold under the name Phlorogine® by the supplier Biotechmarine;

mixtures of extracts from pimpernel roots (*sanguisorba officinalis/poterium officinale*), ginger rhizomes (*zingiber officinalis*) and cinnamon bark (*cinnamomum cassia*), such as that sold under the name Sebustop® by the supplier Solabia;

clove extract, such as that sold under the name Clove extract Powder by the supplier Maruzen;

lactic protein filtrates, such as that sold under the name Normaseb® by the supplier Sederma;

extracts from meadowsweet (*spiraea ulmaria*), such as that sold under the name Cytobiol® Meadowsweet by the supplier Libiol;

sebacic acid, especially that sold in the form of a sodium polyacrylate gel under the name Sebosoft® by the supplier Sederma;

glycine grafted onto an undecylene chain, such as that sold under the name Lipacide UG OR by the supplier Seppic;

trialkyl(C12-C13) citrate sold under the name COSMACOL® ECI by the supplier Sasol; trialkyl(C14-C15) citrate sold under the name COSMACOL® ECL by the supplier Sasol;

10-hydroxydecanoic acid, and especially mixtures of 10-hydroxydecanoic acid, sebacic acid and 1,10-decandiol, such as that sold under the name Acnacidol® BG by the supplier Vincience;

and mixtures thereof.

Preferably, the anti-seborrheic agent active ingredient is selected from:

zinc salts, such as zinc gluconate, zinc pyrrolidone carboxylate (or zinc pidolate), zinc lactate, zinc aspartate, zinc carboxylate, zinc salicylate, zinc cysteate; and preferably zinc pyrrolidone carboxylate (or zinc pidolate) or zinc salicylate;

clove extract, such as that sold under the name clove extract powder by the supplier Maruzen;

glycine grafted onto an undecylene chain, such as that sold under the name Lipacide UG OR by the supplier Seppic;

trialkyl(C12-C13) citrate sold under the name COSMACOL ECI by the supplier Sasol; trialkyl(C14-C15) citrate sold under the name COSMACOL® ECL by the supplier Sasol;

and mixtures thereof.

The anti-seborrheic agent active ingredient is, for example, present in an amount of 0.1% to 10% by weight, preferably 0.1% to 5% by weight, and preferably 0.5% to 3% by weight relative to the total composition weight.

The composition may also include a self-tanning agent.

Self-Tanning Agents

Examples of self-tanning agents that may in particular be mentioned are: dihydroxyacetone (DHA), erythrulose, and the association of a catalytic system formed by salts and oxides of manganese and/or zinc, and alkali and/or alkaline-earth bicarbonates.

The self-tanning agents are generally selected from mono- or poly-carbonyl compounds, examples of which are isatin, alloxan, ninhydrin, glyceraldehyde, mesotartaric aldehyde, glutaraldehyde, erythrulose, derivatives of pyrazolin-4,5-diones such as those described in patent applications FR 2 466 492 and WO 97/35842, dihydroxyacetone (DHA), derivatives of 4,4-dihydroxypyrazolin-5-ones such as those described in patent application EP 903 342. Preferably, DHA is used.

The DHA may be used in the free and/or encapsulated form, for example in lipid vesicles such as liposomes, especially as described in application WO 97/25970.

The composition may include a moisturizing or humectant agent.

Moisturizing or Humectant Agents

Particular humectant or moisturizing agents that may be mentioned are glycerol and its derivatives, urea and its derivatives especially Hydrovance® from the supplier National Starch, lactic acids, hyaluronic acid, AHAs, BHAs, sodium pidolate, xylitol, serine, sodium lactate, ectoine and its derivatives, chitosan and its derivatives, collagen, le plankton, an *imperata cylindra* extract sold under the name Moist 24® by the supplier Sederma, homopolymers of acrylic acid such as Lipidure-HM® from the supplier NOF Corporation, beta-glucan and in particular sodium carboxymethyl beta-glucan from the supplier Mibelle-AG-Biochemistry; a mixture of oils from passiflora, apricot, corn, and rice sold by the supplier Nestlé under the name NutraLipids®; a C-glycoside derivative such as those described in application WO 02/051828 and in particular C-β-D-xylopyranoside-2-hydroxy-propane in the form of a 30% by weight solution of active substance in a water/propylene glycol mixture (60/40% by weight), such as the product produced by the supplier CHIMEX under the name "MEXORYL SBB®"; a musk rose oil sold by the supplier Nestlé; a zinc-enriched *Prophyridium cruentum* algae extract from the supplier Vincience sold under the name Algualane Zinc®; collagen and chondroitin sulfate spheres of marine origin (Ateocollagen) sold by the supplier Engelhard Lyon under the name "sphères de comblement marines"; hyaluronic acid spheres such as those sold by the supplier Engelhard Lyon; and arginine.

The composition may include an active ingredient for the area around the eyes. The applicator that is preferably used with such a composition is described in more detail below.

Agents for the Area Around the Eyes

The agent for the area around the eyes may be an agent encouraging skin microcirculation.

The active ingredient acting on skin microcirculation may be used to prevent fading of the skin and/or to improve the appearance of the area around the eyes, in particular to reduce dark rings. It may, for example, be selected from a maritime pine bark extract such as Pycnogenol® from the supplier Biolandes, manganese gluconate (Givobio GMn® from the supplier Seppic), an *Ammi visnaga* extract such as Visnadine from the supplier Indena, a lupin extract (Eclaline® from the supplier Silab), a hydrolyzed wheat protein/palmitic acid coupled with palmitic acid such as Epaline 100 from the supplier Laboratoires Carilene, Seville orange flower extract (Remoduline® from the supplier Silab), vitamin P and its derivatives such as sodium methyl-4 esculetol mono-ethanoate sold under the name Permethol® by the supplier Sephytal, extracts from ruscus, from horse chestnut, from ivy, from ginseng and from melilot, caffeine, nicotinate and its derivatives, lysine and its derivatives such as Asparlyne® from the supplier Solabia, a black tea extract such as Kombuchka from the supplier Sederma; rutine salts: a *corallina officinalis* algae extract such as that sold par CODIF; and mixtures thereof.

Preferred agents encouraging skin microcirculation that may be mentioned are caffeine, a Seville orange flower extract, a black tea extract, rutine salts, and a *corallina officinalis* algae extract.

The composition may include a slimming agent.

Slimming Agents

Examples of slimming agents (lipolytics) that may be mentioned are caffeine, theophylline and its derivatives, theobromine, sericosine, asiatic acid, acefylline, aminophylline, chloroethyltheophylline, diprofylline, diniprophylline, etamiphylline and its derivatives, etofylline, proxyphylline; extracts from tea, coffee, guarana, maté, cola (*Cola Nitida*) extracts and in particular the dry guarana fruit extract (*Paulina sorbilis*) containing 8% to 10% of caffeine; extracts from common ivy (*Hedera Helix*), from arnica (*Arnica Montana* L), from rosemary (*Rosmarinus officinalis* N), from marigold (*Calendula officinalis*), from sage (*Salvia officinalis* L), from ginseng (*Panax ginseng*), from hypericum (*Hypericum Perforatum*), from broom (*Ruscus aculeatus* L), from meadowsweet (*Filipendula ulmaria* L), from big flowered Java tea (*Orthosiphon Staminicus Benth*), from birch (*Betula alba*), from cecropia and from the argan tree; *ginkgo biloba* extracts, extracts from horsetail, extracts from escine, cangzhu extracts, *chrysanthellum indicum* extracts, extracts from dioscoreae rich in diosgenin or diosgenin or pure hecogenin and their derivatives, extracts from Ballote, extracts from *Guioa*, from *Davallia*, from *Terminalia*, from *Barringtonia*, from *Trema*, from *Antirobia*, Seville orange pip extracts cocoa bean rind extract (*theobroma cacao*) such as that sold by the supplier Solabia under the name Caobromine®.

Sunscreens

The composition may comprise a sunscreen, alone or in combination with other active ingredients.

The sunscreen may be selected from UV screens and their mixtures.

The UV screen may be a chemical or a physical screen or a mixture of such screens.

By way of non-limiting illustration, the following families may be mentioned (the names correspond to the CTFA nomenclature for screens):

anthranilates, in particular menthyl anthranilate; benzophenones, in particular benzophenone-1, benzophenone-3, benzophenone-5, benzophenone-6, benzophenone-8, benzophenone-9, benzophenone-12, and preferably Benzophenone-2 (Oxybenzone), or Benzophenone-4 (Uvinul MS40 from the supplier B.A.S.F.); benzylidene-camphors, in particular 3-benzylidene-camphor, benzylidenecamphosulfonic acid, camphor benzalkoniummethosulfate, polyacrylamidomethylbenzylidene camphor, terephthalylidene dicamphor sulfonic acid, and preferably 4-methylbenzylidene camphor (Eusolex 6300 from the supplier Merck); benzimidazoles, in particular benzimidazilate (Neo Heliopan AP from the supplier Haarmann and Reimer), or phenylbenzimidazole sulfonic acid (Eusolex 232 from the supplier Merck); benzotriazoles, in particular drometrizole trisiloxane, or methylene bis-benzotriazolyltetramethylbutylphenol (Tinosorb M from the supplier Ciba); cinnamates, in particular cinoxate, DEA methoxycinnamate, diisopropyl methylcinnamate, glyceryl ethylhexanoate dimethoxycinnamate, isopropyl methoxycinnamate, isoamyl cinnamate, and preferably ethocrylene (Uvinul N35 from the supplier B.A.S.F.), octylmethoxycinnamate (Parsol MCX from the supplier Hoffmann La Roche), or octocrylene (Uvinul 539 from the supplier B.A.S.F.); dibenzoylmethanes, in particular butyl methoxydibenzoylmethane (Parsol 1789); imidazolines, in particular ethylhexyl dimethoxybenzylidene dioxoimidazoline; PABAs, in particular ethyl dihydroxypropyl PABA, ethylhexyldimethyl PABA, glyceryl PABA, PABA, PEG-25 PABA, and preferably diethylhexylbutamido-triazone (Uvasorb HEB from the supplier 3V Sigma), ethylhexyltriazone (Uvinul T150 from the supplier B.A.S.F.), or ethyl PABA (benzocaine); salicylates, in particular dipropyleneglycol salicyclate, ethylhexyl salicylate, homosalate, or TEA salicylate; triazines, in particular anisotriazine (Tinosorb S from the supplier Ciba); drometrizole trisiloxane, zinc oxide, titanium dioxide, coated or uncoated zinc oxide, iron oxide, zirconium oxide or cerium oxide.

The quantity of screens depends on the desired final use. It may, for example, be from 1% to 20% by weight and preferably from 2% to 10% by weight relative to the total composition weight.

Active Ingredients Encouraging Regrowth and/or Limiting Hair Loss

The composition may include an active ingredient encouraging regrowth and/or limiting hair loss. In particular, these additional compounds are selected from lipoxygenase inhibitors, bradykinin inhibitors, prostaglandins and their derivatives, agonists or antagonists for prostaglandin receptors, non-prostanoic analogs of prostaglandins, and mixtures thereof.

Examples of additional compounds encouraging hair growth that may be present in the composition of the invention that may be mentioned are vasodilators, antiandrogens, cyclosporins and their analogs, antimicrobials and antifungals, anti-inflammatories, and retinoids, used alone or as a mixture.

In particular, the vasodilators that may be used are potassium channel agonists including minoxidil, cromakalim, nicorandil and diaxozide, used alone or in combination.

Particular antiandrogens that may be used include steroid or non-steroid inhibitors of 5-α-reductase, such as finasteride, cyprosterone acetate, azelaic acid, its salts and its derivatives, flutamide, oxendolone, spironolactone, and diethylstilbestrol.

The antimicrobial or antifungal compounds may be selected from selenium derivatives, octopirox, triclocarban, triclosan, zinc pyrithione, itraconazole, asiatic acid, hinokitiol, mipirocine, tetracyclins, especially erythromycin, clinycin hydrochloride, benzoyl or benzyl peroxide, minocyclin and compounds belonging to the imidazoles such as econazole, ketoconazole or miconazole or their salts, esters of nicotinic acid, especially tocopherol nicotinate, benzyl nicotinate and $C_1$-$C_6$ alkyl nicotinates such as methyl or hexyl nicotinates.

The anti-inflammatories may be selected from steroidal anti-inflammatories steroids such as glucocorticoids, corticosteroids (for example: hydrocortisone) and non-steroidal anti-inflammatories such as glycyrrhetinic acid and α-bisabolol, benzydamine, or salicylic acid.

The retinoids may be selected from isotretinoin, acitretin and tazarotene.

Other additional active compounds for encouraging the growth and/or limiting hair loss that may be used in a composition according to the present invention that may be mentioned are aminexil, 6-0-[(9Z,12Z)-octadeca-9,12-dienoyl] hexapyranose, benzalkonium chloride, benzethonium chloride, phenol, estradiol, chlorpheniramine maleate, chlorophylline derivatives, cholesterol, cysteine, methionine, menthol, peppermint oil, calcium panthotenate, panthenol, resorcinol, protein kinase C activators, glycosidase inhibitors, glycosaminoglycanase inhibitors, pyroglutamic acid esters, hexosaccharidic or acyl-hexosaccharic acids, substituted aryl ethylenes, N-acyl amino acids, flavonoids, derivatives and analogs of ascomycin, histamine antagonists, saponins, proteoglycanase inhibitors, estrogen agonists and antagonists, pseudoterins, cytokines and growth factor promoters, IL-1 or IL-6 inhibitors, IL-10 promoters, TNF inhibitors, benzophenones and hydantoin, retinoic acid; vitamins such as vitamin D, analogs of vitamin B12 and panthotenol; triterpenes such as ursolic acid; antipruritics such as thenaldine, trimeprazine or cyproheptadine; antiparasitics, in particular metronidazole, crotamiton or pyrethrinoids; calcium antagonists, such as cinnarizine, diltiazem, nimodipine, verapamil, alverine or nifedipine; hormones such as estriol or its analogs, thyroxine and its salts, progesterone; FP receptor antagonists (type F prostaglandin receptors) such as latanoprost, bimatoprost, travoprost, or unoprostone; 15-hydroxyprostaglandin desydrogenase inhibitors; and mixtures thereof.

Anti-Acne Active Ingredients

The composition may include anti-acne active ingredients such as salicylic acid or benzoyl peroxide, octopirox, dextrogyratory and levogyratory sulfur-containing amino acids, their salts and their N-acetylated derivatives such as N-acetylcysteine.

The composition may contain, as a cosmetic active ingredient, an additional hydrophobic active ingredient selected from polyols, urea, allantoin, sugars and sugar derivatives, hydrosoluble vitamins, plant extracts (from Iridaceae or soybean, algae extracts) and/or an additional lipophilic active ingredient selected from essential fatty acids, ceramides, essential oils, phospholipids such as lecithin, and mixtures thereof.

Other examples of active ingredients that may be suitable for carrying out the present invention include fresheners, deodorants, anti-perspirants, analgesics, anesthesics, antibacterials, anti-yeasts, anti-virals, anti-dermatitis agents, anti-pruritics, anti-hemetics, antioxidants such as green tea or active fractions thereof, vascular protectors, travel sickness combating agents, anti-irritants, anti-inflammatories, immunomodulators, anti-hyperkeratolytics, for the treatment of dry skin, anti-psoriatics, anti-seborrheics, anti-asthmatics and bronchodilators, UV protectors, anti-histaminics, healing agents, cortico-steroids, tanning agents, and mixtures thereof.

The quantity of active ingredients in the application element and/or in the composition may be adjusted as a function of the treated region and of the intended aim.

Microorganisms

The composition of the invention may include microorganisms.

The microorganism or microorganisms may be included in the composition in the live, semi-active or inactivated, dead, form. They may also be included in the form of fractions of cellular components or in the form of metabolites. The microorganism or microorganisms, metabolite(s) or fraction(s) may also be introduced in the form of a lyophilized powder, a culture supernatant and/or, if necessary, in a concentrated form. It may be advantageous to use these microorganisms in an inactivated or even dead form.

Applicator Element

The applicator element may comprise a porous, fibrous, or cellular substrate that is optionally permeable to the composition, optionally composite, and in particular selected from woven and non-woven felts, with or without portions in relief that are visible to the naked eye. The applicator element may include flocking.

The applicator element may carry a cosmetic or dermatological composition impregnating the substrate in depth or on the surface. In a variant, the applicator element need not carry any composition before it is assembled on the handpiece.

The applicator element may be elastically deformable and/or compressible.

The applicator element may comprise a foam. The foam may be based on synthetic or natural material. By way of example, the foam may have open cells. The foam may have density greater than or equal to 30 kilograms per cubic meter ($kg/m^3$). The foam may be made of a material selected from the following list: polyurethane, polyether, polyester, polyvinyl chloride, polyethylene, ethylene vinyl acetate (EVA), latex, silicone, sytrene-isoprene-sytrene (SIS), sytrene-ethylene-butadiene-sytrene (SEBS), silicon elastomer, latex elastomer, nitril elastomer, butyl elastomer, Neoprene®, nitrile rubber (NBR), sytrene-butadiene-rubber (SBR), this list not being limiting.

The applicator element may include a thermocompressed foam. Thermocompression serves to create portions in relief at the surface of the foam and/or to laminate it with an elastic fabric, thus making it possible to retain the flexibility of the foam while also having the feel of a textile that is more agreeable than the feel of plastics material.

By way of example, the applicator element may comprise a hydrophilic cured polyester foam, e.g. having density equal to 32 $kg/m^3$.

An example of thermocompressed foam is a closed-cell foam made of polyolefin, e.g. polyethylene, that is thermocompressed to have a density of 33 kg/m³, and that is for example laminated with an elastic fabric, such as Lycra®, for example.

The foam may be a foam that is soft and flexible and that is particularly suitable for spreading the composition, sometimes also referred to as a sponge, for example.

A sponge as used traditionally for applying foundations may for example be made of Yukilon® from the supplier Penthouse Group.

The applicator element may present a composite structure having a plurality of layers, optionally of different kinds, e.g. a plurality of types of foams or of non-woven fabric, or of films.

By way of example, the various layers may include different active agents.

The applicator element may include at least one metal-plated layer, a film, a net, synthetic or natural fibers, e.g. fiber derived from corn (maize), fibers of hemp, of flax, of cotton, of jute, of kenaf, of raffia, of ramie, of *Paja Toquilla*, of sisal, of reed, of rush, of alfa, of phormium, of coir, of wool, of silk, of soy beam, of Manila, of kumazasa, of persimmon, of kapok, of burdock, of cereals, or of bamboo.

The applicator element may include biocellulose, used in pure form or in a form combined with fibers of other types, e.g. fibers of natural origin. The biocellulose fibers may be free or bonded together and/or bonded to other fibers. The biocellulose may be used in sheet form, e.g. obtained by compacting a culture of biocellulose fibers, after they have been rinsed.

The applicator element may also include magnetic or magnetizable particles, e.g. for the purpose of improving microcirculation.

The applicator element may be perforated, e.g. to allow light to pass through the applicator during treatment.

Sets

The invention also provides a set comprising one or more applicators as defined above, and an electrical appliance enabling energy, high temperature, or low temperature to be transmitted to the applicator mounted on the handpiece. Such a set may be offered to users within a kit, in a common package.

Where appropriate, the set proposed to consumers comprises a handpiece and a plurality of applicators, which applicators may be identical or otherwise and may optionally contain the same composition. The applicators may be contained independently of one another in individual packaging, or within a common package, e.g. in a stack.

When the set includes a plurality of applicators, at least two applicator elements may be arranged to perform treatments that are different.

At least two applicators may be different but include the same cosmetic composition. For example, the applicators may differ in their shape or their texture.

With packaging arranged to receive a plurality of applicators, the packaging may possibly contain only identical applicators.

Appliance

Other exemplary embodiments of the invention provide a handpiece arranged to perform treatment, e.g. cosmetic or therapeutic treatment, the handpiece including a reader arranged to receive releasably an applicator including an encoder capable of co-operating with the reader. The operation of the handpiece is conditioned at least on reading the encoder.

The handpiece includes a module as defined above in order to modify the temperature of the applicator, and/or the treated region and/or to transmit energy to the applicator, and/or to the treated region.

By way of example, the handpiece may include a heater resistance or a piezoelectric element that is positioned under the applicator element when the applicator is in place.

Applicator

Other exemplary embodiments of the invention provide a single-use applicator carrying a cosmetic or dermatological composition for application to keratinous materials, the applicator including an encoder and being capable of being removably fastened to a handpiece, as defined above. The applicator may include an applicator element of the invention, which may optionally be pre-impregnated. The applicator may include an encoder so that it is present on the handpiece while it is in use.

When the handpiece is capable of receiving information for controlling its operation from a base station, the applicator may be associated with an encoder that is present only at the base station while the handpiece is in use.

By way of example, the applicator may include an encoder that is separable from an applying portion that is mounted on the handpiece and packaged together therewith in the same packaging. On opening the packaging, the user may place the encoder on the base station and the applying portion on the handpiece. The base station transmits information to the handpiece for controlling its operation.

BRIEF DESCRIPTION OF THE DRAWINGS

The invention can be better understood on reading the following detailed description of non-limiting embodiments thereof, and on examining the accompanying drawings in which:

FIG. 4 is a diagrammatic and fragmentary axial section view of an applicator;

FIG. 5 is a plan view of the FIG. 2 handpiece without an applicator;

FIG. 6 is a fragmentary longitudinal section view on VI-VI of the FIG. 2 handpiece;

FIG. 7 shows applicators made so as to be stackable;

FIGS. 8*a* to 8*d* are fragmentary and diagrammatic axial sections showing examples of co-operation between the encoder and the reader; and FIG. 9 is an exploded view in perspective showing another example of fastening the applicator on the handpiece.

MORE DETAILED DESCRIPTION

Figure 1:
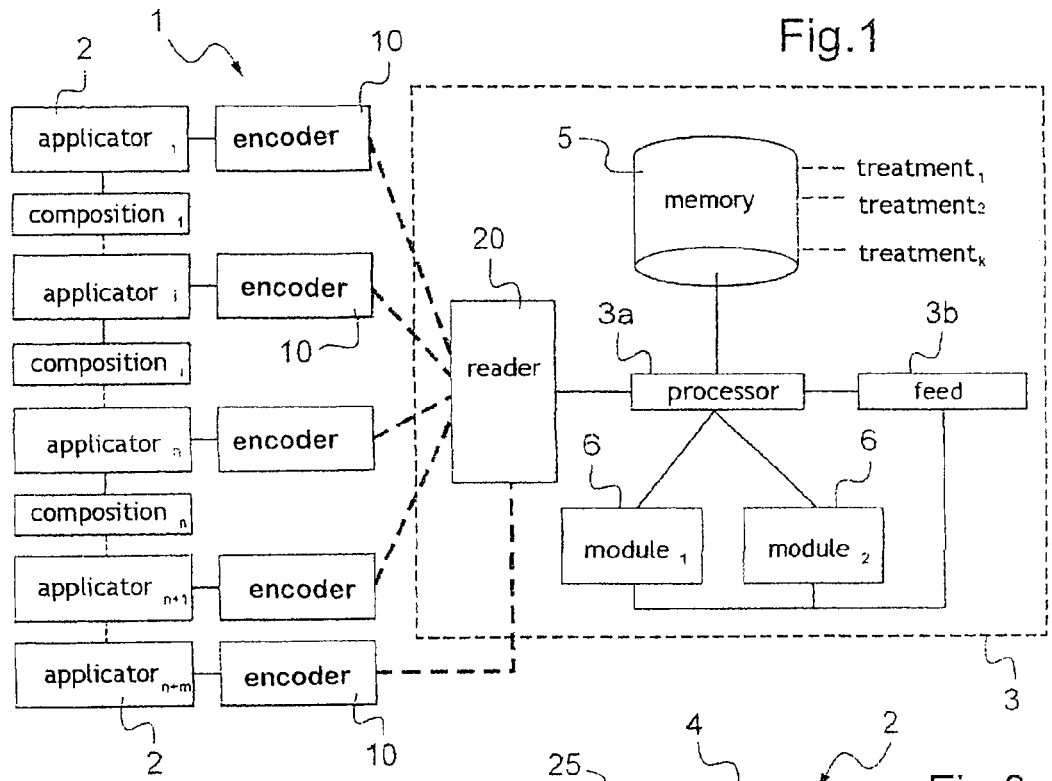
FIG. 1 is a block diagram of an example set of the invention.

FIG. 1 shows an example device 1 of the invention, comprising firstly an electrical appliance in the form of a handpiece 3, and secondly an applicator 2 that may optionally be selected from a range of set 2 of N applicators, e.g. different applicators already filled with respective compositions and/or different applicators that are not filled with respective compositions, but that are used as application or treatment tools on human keratinous materials.

The electrical appliance 3 is arranged to read at least one item of information associated with an applicator mounted on the handpiece, e.g. in order to perform treatment that is specific to the applicator used with the handpiece.

The applicator 2 thus includes an encoder 10 for encoding the information, and the electrical appliance 3 includes reader 20 arranged to read the information conveyed by the encoder 10.

The appliance 3 may include any processor 3a suitable for determining at least one operating parameter of the handpiece as a function of the information read, the processor possibly being associated with a memory 5, which is shown as being separate from the processor 3a in FIG. 1, but which could be internal thereto.

The appliance 3 includes an electrical power supply 3b that may be of any type, in particular of a self-contained type and incorporated in the handpiece, or else of a type that is connected to an electricity network.

The handpiece 3 may include one or more treatment modules 6 that may be activated selectively as a function of the information read, when the handpiece 3 is made so as to be capable of subjecting an applicator to stimuli that differ as a function of the information read, e.g. subjecting the applicator to high or low temperature, or to vibration or to light, as described in greater detail below.

A treatment module, or indeed the treatment module when there is only one of them, may be controlled by the processor 3a as a function of the information read. For example, the treatment module may be arranged to heat the applicator to a predetermined temperature as a function of the information read.

In an example, the handpiece 3 includes only one heater module 6, with the operation thereof depending on the information read by the reader. For example, the reader may determine the degree of heating and/or the shape of the heating curve.

The processor 3a may include any analog or digital electronic circuit that enables comparison operations and/or calculations to be performed, and in particular it may include any microprocessor, microcontroller, programmable logic array, . . . .

The processor 3a may form a permanent part of the appliance 3 or it may be releasably fastened thereto, thus enabling the user to use a personal digital assistance (FDA), a mobile telephone, or some other appliance of sufficient calculation power to be used as the processor.

The processor 3a may also subcontract all or some of the calculations to a remote appliance, e.g. a microcomputer, a PDA, or a mobile telephone, with information exchange possibly taking place by radio, e.g. using a Bluetooth, WiFi, or infrared connection.

Where appropriate, the processor 3a may comprise no more than an interface enabling information for processing to be transmitted remotely and for receiving said information in return after processing, and suitable for controlling the module(s) in compliance with the information as returned.

Reader/Encoder Association

Various encoder may be associated with various reader.

For example, the encoder may be tactile and the reader may comprise one or more feelers that respond to the encoder.

In particular exemplary embodiments, the encoder comprise tabs, projections, or other portions in relief of length, and/or arrangement, and/or number that encodes information, and the reader may comprise one or more microswitches, e.g. membrane switches, or pushbuttons or reed type switches, that are actuated by the tabs, projections, magnets, or other portions in relief of the encoder.

Figure 2:
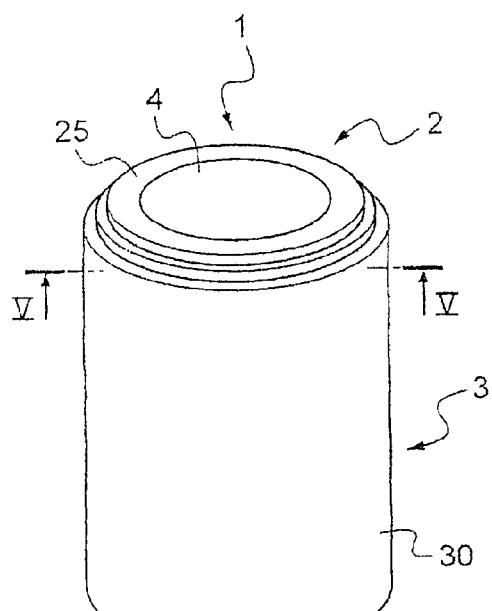
FIG. 2 is a diagrammatic and fragmentary perspective view of an example of a device made in accordance with the invention.

In the example of FIG. 2, there can be seen a handpiece 3 arranged to receive an applicator 2. The handpiece 3 comprises a cylindrical body 30, however the handpiece could be of some other shape, which shape is preferably ergonomic.

The applicator 2 comprises an applicator element 4 surrounded by a frame 25 and it includes tabs 10 of presence, location, and/or length suitable for encoding information.

The handpiece 3 may include housings (not visible in FIG. 2) in which the tabs may be engaged when present, and the tabs may act on switches 20 placed in the bottoms of said housings, as shown in FIG. 6.

The handpiece 3 may be arranged to detect a change of state in the switches, thus enabling information to be encoded in binary form. The number of values that can be encoded in this way depends on the number of tabs.

In an example, the frame may have three tabs, which may be present or absent. The handpiece has three corresponding switches. The operating logic may be as follows:

| Tabs (0 = absence, 1 = present) | | | |
| --- | --- | --- | --- |
| 1 | 2 | 3 | Action |
| 0 | 0 | 0 | No operation |
| 1 | 0 | 1 | Heat to T1 |
| 1 | 1 | 0 | Heat to T2 |
| 1 | 1 | 1 | Heat to T3 |

Where appropriate, the encoder, when implemented in the form of tabs, projections, or other portions in relief, may participate in fastening the applicator on the handpiece. For example, the tabs may snap-fasten with the handpiece or they may retain the applicator by friction. In a variant, such fastening may be performed independently of the encoder.

In variant exemplary embodiments, the handpiece includes feelers that are pushed in or not as a function of the presence or absence of openings or recesses in the applicator and located in register with the feelers.

The encoder may also be mechanical, with the reader being optical. For example, the applicator may include portions in relief or other projections that mask or do not mask photoreceivers, depending on the encoding.

The encoder and reader may both be optical, and the applicator may include printing that can be read by photoreceivers present on the handpiece.

The encoder may also include magnetic elements in a configuration that serves to encode information, the handpiece possibly including Hall effect or induction sensors for detecting the presence or absence of such magnetic elements.

The applicator may include electrical elements, e.g. elements that are resistive, capacitive, or inductive, and the handpiece may be arranged to detect an electrical magnitude associated with said elements, e.g. after an electrical connection has been established between the applicator and the handpiece.

The applicator may include an array of resistors or diodes connected to electrical contacts that co-operate with other contacts present on the handpiece and that enable the encoded information to be read by reading the array of resistors or diodes.

The applicator may also include an electronic memory of contacts that may be read by a wire connection via contacts that are formed on the applicator and on the handpiece, or via a wireless connection, e.g. by using an RFID chip or by using an optical connection, e.g. an infrared connection.

The information that is encoded by the encoder on an applicator may be an identifier for the applicator. Under such circumstances, the handpiece may have a memory that contains operating parameters to be applied, or it may look these operating parameters up on a remote server, e.g. via an Internet or Intranet connection.

The applicator may also include an encoder that encode all or part of the operating parameters themselves; for example, the encoder may encode an operating temperature for the handpiece, an operating duration, whether or not to apply a source of vibration, whether or not to apply an electrical voltage, this list not being limiting.

The applicator may also contain as information a link that refers the appliance to a server where it may download said operating parameters.

The applicator may also act via the information encoded by the encoder to inform the electrical appliance about the nature of the composition presented on the applicator, and the electrical appliance may include predefined operating parameters in memory that vary as a function of various compositions. For example, the applicator may inform the appliance that it is carrying a cleaning, care, or makeup composition, and the appliance may have operating parameters that differ depending on whether the composition relates to cleaning, care, or makeup.

When each identifier is specific to one applicator, the appliance may be arranged to prevent the same applicator being reused after said applicator has been used for a determined length of time or for a given number of uses.

For example, a set of sixteen applicators may be provided in a single package, with each of the sixteen applicators being associated with a unique identifier selected in the range 1 to 16, e.g. by means of four tabs serving to encode $2^4$ different values.

The appliance may measure the amount of utilization time that has elapsed with a given applicator mounted thereon, and after a predetermined duration has elapsed it may inform the user that it is necessary to change the applicator and/or it may prevent operation of the handpiece even if the applicator continues to be used. The user is thus caused to replace the applicators progressively as they are used up.

When the reader and fastener of the applicator make this possible, a single applicator may have encoders associated with two opposite faces, each of which is suitable for use in performing a treatment. This may enable the user to begin by using one face of the applicator and then, after one or more uses, to turn the applicator over on the handpiece in order to benefit from a new surface for use. Under such circumstances, the appliance may, for example, measure the duration of use of each face and inform the user that it is time to turn the applicator over. By way of example, each applicator face may be associated with specific encoder that enable the handpiece to recognize which face is being used.

By way of example, a single applicator may also have two faces that present application characteristics that are different or that are loaded with compositions that are different, and depending on which face is used, the operating parameters of the handpiece may be different. The handpiece may recognize which face is being used and adjust the parameters accordingly.

Applicator

As shown in FIGS. 3a to 3d, the applicator may comprise a central applicator element that is held at its periphery by a support frame 25.

The applicators shown in FIGS. 3a to 3d may be usable with the handpiece of FIG. 2. The encoder in this example comprises one to three tabs 10 situated on the frame 25 of the applicator, e.g. each at a different distance from the edge, so as to provide keying means.

Figure 3A:
FIGS. 3*a* to 3*d* are perspective views showing in isolation example applicators that may be mounted on the handpiece of FIG. 2.
Figure 3B:
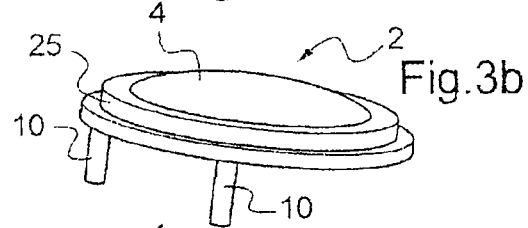
Figure 3C:
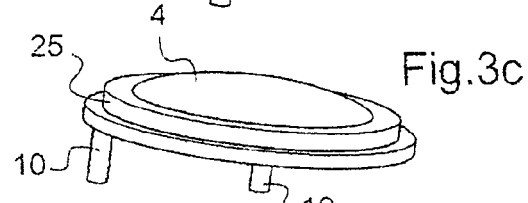
Figure 3D:
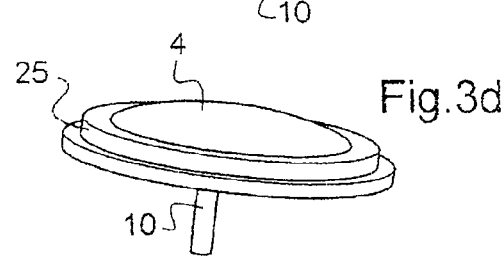

The applicator shown in FIG. 3a has three tabs, while the applicators shown in FIGS. 3b and 3c have two tabs each, whereas the applicator shown in FIG. 3d has only one tab. The tabs are suitable for being engaged in the housings of the handpiece, there being three of these housings, as shown in FIG. 5, and they may act on reader in said housings.

As shown in FIG. 4, the frame 25 of the applicator may comprise two annular portions 25a and 25b that overlap at least in part and that are fastened to each other, with the applicator element 4 being inserted between them.

The two annular portions 25a and 25b are separately molded out of thermoplastic material, for example, and they are subsequently assembled together, or else they may be molded as a single part and they may be connected together by a film hinge, with one of them being folded down onto the other while the applicator member is being assembled in order to hold the applicator element captive between them.

The tabs may be hollow so as to enable the applicators to be stacked, as shown in FIG. 7.

By way of example, the two annular portions may be fastened together by snap-fastening or by using adhesive or heat-sealing, in particular ultrasound sealing or by staking, screw-fastening, crimping, or stamping.

Naturally, the use of a frame merely constitutes one possible example amongst others of means suitable for holding an applicator element or a block of composition on the handpiece, and for example the handpiece may comprise a stem carrying a block of composition. Under such circumstances, the encoder may be formed on the stem. By way of example, the stem may have means for fastening to the handpiece and a portion of greater or shorter length that penetrates to a greater or lesser extent into a housing of the handpiece once fastened thereto, thereby encoding the information.

The applicator element may also be made by flocking a portion of a part that is configured for fastening on the handpiece, and that may be made integrally by molding a thermoplastic material, with the flocked portion being made of elastomer, for example.

Where appropriate, the applicator may include a reservoir containing the composition, which reservoir communicates with the applicator element.

The applicator may also include a metal layer suitable for heating, cooling, or performing a massaging action on human keratinous materials. Such a layer may optionally come into direct contact with the skin.

Where appropriate, the applicator may also serve as an electrode, for electrophoresis or iontophoresis treatment.

The applicator may present abrasive properties in order to remove at least some of the dead cells on the surface of the skin. Such applicators are obtained either by taking a substantially rigid cellular material, or by incorporating hard grains in a flexible cellular material. An example of an abrasive surface is an exfoliating pad of non-woven material sold by the supplier 3M.

The handpiece may be used with applicators that are filled with composition, and also with other applicators that are not used for applying composition but that serve to perform cosmetic or dermatological treatments that do not require composition to be applied, for example massaging, electrical stimulation, or phototherapy treatments.

Once the applicator is in place on the handpiece, the operating parameters for the handpiece may be selected in a manner that is entirely automatic.

In a variant, the appliance may have an interface enabling the user to take cognizance of at least one preselected operating parameter, as a function of the information read by the reader, and the user may have the option of confirming the selection made by the appliance or of modifying the operating parameters.

The handpiece may benefit from an interface enabling its memory and/or the program controlling its operation to be updated, e.g. by reading memory cards or a universal serial bus (USE) port, etc.

Where appropriate, the surface used for application may be covered in a removable protective film 45.

The set of applicators made available may be contained in a sealed package. In a variant, the handpiece is provided with a plurality of applicators that are individually packaged, e.g. each in its own sealed package. An appliance may have an applicator element that is wet since it is pre-impregnated with a liquid composition.

In a variant, the applicator element may carry a composition in the anhydrous state and the applicator may need to be moistened prior to use, e.g. by pouring water or any other appropriate solvent thereon.

Applicators may be proposed to users in the form of a plurality of identical applicators within a common package or, in a variant, as an assortment of different applicators within a common package.

In another embodiment, the reader comprises mechanical feelers, as shown in FIGS. 8a to 8d.

FIGS. 8a-8d show the different encoders 10 that may correspond to different applicators, combined with the same reader 20. The encoder comprises, for example, studs in the form of half-cones that are truncated and hollow and that present shapes that differ depending on the values to be encoded.

In FIGS. 8c and 8d, the encoders are studs in the form of chamfered cones and the reader comprises two series of diametrically-opposite sensors.

In the example shown, the reader comprises three sensors each situated at a different distance from the opening of the stud-receiving housing.

The handpiece shown in FIG. 9 has a removable ring 50 arranged to screw onto the body of the handpiece 3 and hold the applicator on the handpiece.

Modules

As mentioned above, the handpiece may include a treatment module capable of taking up a plurality of operating states as a function of information read from the applicator.

When the treatment module comprises heater means, as shown in FIG. 5, it may for example comprise a resistor element 61 that conveys a current so as to heat a surface 60 situated under the applicator element, or so as to heat the block of composition, if any, when the applicator is in position, in order to reach a predefined temperature.

This temperature may be detected by a temperature sensor, and the handpiece may include a regulation loop enabling the surface temperature to be maintained at a predefined value. The surface 60 may come into contact with the inside face of the applicator when the applicator is fastened on the handpiece, and heat may be conveyed by conduction to the outside surface of the applicator, i.e. the surface that is used for applying the composition.

The surface 60 may be defined by a metal plate.

The handpiece may include a processor module that is suitable for handling both high temperatures and low temperatures, by means of a Peltier effect component. Depending on the current flow direction, such a component presents a face that heats up or cools down. Such a Peltier effect component may, for example, be placed touching a metal plate that rests against the inside face of the applicator element.

As mentioned above, the handpiece may include other treatment modules, e.g. for transmitting ultrasound or light energy to the keratinous materials being treated.

Treatment Methods

A first implementation of the invention may consist in mounting an applicator on the handpiece, the applicator carrying a composition, and then in bringing the applicator mounted in this way on the handpiece into contact with the materials to be treated.

The duration of the treatment may lie, for example, in the range about 1 minute to about 30 minutes.

In addition to applying the composition, the method may include additional treatments by electrophoresis, iontophoresis, sonophoresis, phototherapy, application of high or low temperature, application of an electrical current, of radiofrequencies, or by magnetophoresis.

In operation, the handpiece uses operating parameters that depend on the information it has read, as encoded in the encoder of the applicator. The parameter may be a temperature to which the applicator is to be heated, for example.

The treatment method may also include an additional step that consists in leaving the composition in contact with keratinous materials, and possibly in rinsing the keratinous materials.

In another implementation of the invention, the applicator mounted on the handpiece does not include any composition, and composition is applied to the keratinous materials prior to using the applicator. The applicator is nevertheless recognized by the electrical appliance, thus enabling it to adjust automatically at least one operating parameter, e.g. the temperature of the applicator.

The user may make use of the applicator as mounted on the handpiece to apply composition and/or to cause composition to penetrate.

The composition may be delivered in the same packaging as the applicator and/or the handpiece.

The appliance may stop automatically or under manual control. For example it may suffice to remove the applicator in order to switch off the appliance.

Proposed Example

The handpiece comprises a heater module having a metal disk, e.g. an aluminum disk, with a surface area of 20 square centimeters ($cm^2$), and with a heater resistor secured to the disk, an electrical power supply, and a system for fastening the applicator against the aluminum surface. The processor and the power supply (optionally-chargeable batteries) are contained in the body of the handpiece.

The applicator includes an applicator element and possesses at least one tab that serves for positioning purposes and that triggers treatment, and two other tabs that encode the temperature rise program.

Once the applicator has been placed on the heater surface and is in contact therewith, the internal program of the processor triggers reading of the information encoded by the other tab(s) or by the encoder.

Depending on the presence or absence of these other tabs, as detected by switches, the type of treatment that is performed differs. In the absence of an applicator, the appliance does not operate.

For example, a single detected tab corresponds to applying a temperature of 35° C. followed by stabilization during 2 minutes, then by raising the temperature to 40° C. over 1 minute, followed by stopping with a sound "beep" being issued and with a light-emitting diode (LED) being switched off (program 1).

Detecting two tabs corresponds to raising the temperature progressively to 45° C. over a time period of about 4 minutes, with the maximum temperature being maintained for 30 seconds and then switching off with a sound "beep" being emitted and with an LED being switched off (program 2).

| Tabs | | | |
|---|---|---|---|
| 1 | 2 | 3 | |
| 0 | — | — | Off |
| 1 | — | — | Switch on reader |
| 1 | 1 | 0 | Program 1 (applicator 1) |
| 1 | 1 | 1 | Program 2 (applicator 2) |

Applicator Impregnated with a Makeup-Removal Emulsion for Cleaning the Face

The applicator includes a polyurethane foam applicator element impregnated with the following emulsion for cleaning purposes: (proportions are by weight).

| Chemical name | US INCI | Commercial reference | |
|---|---|---|---|
| Allantoin | Allantoin | | 0.05 |
| Potassium chloride | Potassium chloride | | 0.05 |
| Sodium hydroxide | Sodium hydroxide | | 0.065 |
| Disodium salt, ethylene diamine tetracetic acid, 2H$_2$O | Disodium EDTA | | 0.1 |
| Magnesium gluconate | Magnesium gluconate | | 0.02 |
| Sodium chloride | Sodium chloride | | 0.02 |
| Plankton in non-stabilized aqueous dispersion | Vitroscilla fermant | Chimex | 1 |
| A mixture of methyl, ethyl, propyl, butyl, isobutyl, P-hydroxybenzoates and phenoxy-2 ethanol | Phenoxyethanol and methylparaben and ethylparaben and isobutylparaben and butylparaben | Phenotip Clariant | 1 |
| 2-ethylhexyl palmitate | Ethylhexyl palmitate | | 15 |
| Protected shea butter | *Butyrospermum parkii* (shea butter) | | 1 |
| Isononyl isononanoate | Isononyl isononanoate | | 10 |
| Pure bidistilled cetyl alcohol | Cetyl alcohol | | 0.8 |
| Fragrance | Fragrance | | 0.2 |
| Wanthan gum | Wanthan gum | | 0.1 |
| Carboxyvinyl polymer synthesized in a mixture of ethyl acetate and cyclohexane | Carbomer | Carbopol 980, Lubrizol | 0.4 |
| 1,3-butylene glycol | Butylene glycol | | 8 |
| Microbiologically clean deionized water | Water | | 60 |
| Glycerol | Glycerin | | 1 |
| A mixture of glyceryl mono-stearate and (100 EO) polyethylene glycol stearate | Glyceryl stearate and PEG-100 stearate | Simulson 165, Seppic | 0.5 |
| (13 EO/13 PO/13 EO) condensate of ethylene oxide and ethylene oxide oxide 5PM/2900 | Poloxamer 184 | Synperonic Croda | 0.6 |

Applicator Impregnated with a Makeup-Removal Oil for Cleaning the Face

The applicator included a viscose applicator element impregnated with a makeup-removal oil having the following composition:

| Chemical name | US INCI | Commercial reference | |
|---|---|---|---|
| Crystallized sorbitol | Sorbitol | | 3 |
| 2-methyl-4-isothiazoline-3-one 9.5 in water | Methyliso-thiazolinone | | 0.1 |
| 2-ethylhexyl palmitate | Ethylhexyl palmitate | | 4 |
| Dicaprylyl ether | Dicaprylyl ether | | 16 |
| 80/20 copolymer of AMPS and ethoxyl (8 moles) C16/C18 alcohol methacrylate - synthesized in tertio butanol | Acryloyldimethyl taurate/ steareth-8 methacrylate copolymer | Aristoflex SNC, Clariant | 0.7 |
| Microbiologically clean deionized water | Water | | 75.67 |
| Glycerol 2-ethyl hexyl ether [or 3-(ethyl-2 hexyl oxy)-1,2 propanediol] | Ethylhexyl-glycerin | Sensiva SC50, Schulke & Mayr | 0.5 |
| (4 EO) oxyethylene sorbitane mono-laurate | Polysorbate 21 | | 0.03 |

The term "comprising a" should be considered as being synonymous with "comprising at least one" unless specified to the contrary.

What is claimed is:

1. A device for treating human keratinous materials, the device comprising:
   an electrical appliance comprising a handpiece and a reader; and
   an applicator suitable for being removably fastened on the handpiece and comprising:
   i) an applicator element including fibers and/or foam cells suitable for enabling a cosmetic or dermatological composition to be applied on the keratinous materials, the applicator element carrying the cosmetic or dermatological composition prior to being mounted on the handpiece; and
   ii) at least one encoder for encoding information arranged to be read by the reader;
   wherein operation of the handpiece depends on the information read,
   wherein the handpiece is configured to subject the applicator to at least one stimulus selected from: applying heat, applying cold, applying sound or ultrasound, applying a magnetic field, applying electromagnetic radiation, and wherein the handpiece includes a treatment module configured to take up a plurality of operating states as a function of the information read from the applicator.

2. The device according to claim 1, wherein the applicator includes a support on which the encoder is positioned.

3. The device according to claim 1, wherein the encoder comprises at least one of: a magnetic code, an optical code, a bar code, an RFID chip, an electronic chip, a tactile code, an electrical code.

4. The device according to claim 1, wherein the encoder is carried or formed by one or more portions in relief.

5. The device according to claim 1, wherein the appliance is configured to prevent reuse of an applicator after it has been used in predefined conditions.

6. The device according to claim 1, wherein the encoder fastens the applicator on the handpiece.

7. The device according to claim 1, wherein the cosmetic or dermatological composition is a cleaning composition.

8. The device according to claim 1, wherein the encoder encodes at least one operating parameter of the handpiece, or an identifier of the applicator and/or the cosmetic or dermatological composition.

9. The device according to claim 1, wherein the applicator includes a frame made up of two portions that overlap at least in part and that hold the applicator element between the two portions.

10. The device according to claim 1, wherein the handpiece is packaged together with at least two different applicators, the applicators including encoders encoding respective different items of information.

11. A device for treating human keratinous materials, the device comprising:
an electrical appliance comprising a handpiece and a reader; and
an applicator suitable for being removably fastened on the handpiece and comprising:
i) an applicator element including fibers and/or foam cells suitable for enabling a cosmetic or dermatological composition to be applied on the keratinous materials, the applicator element carrying the cosmetic or dermatological composition prior to being mounted on the handpiece; and
ii) at least one encoder for encoding information arranged to be read by the reader;
wherein operation of the handpiece depends on the information read, and
wherein the handpiece includes a heater module and is configured to heat the applicator to a predefined temperature as a function of the information read.

12. A method of cosmetic or therapeutic treatment, the method comprising:
providing a device for treating human keratinous materials, the device comprising an electrical appliance comprising a handpiece and a reader; and an applicator suitable for being removably fastened on the handpiece and comprising an applicator element including fibers and/or cells suitable for enabling a cosmetic or dermatological composition to be applied on the keratinous materials; and at least one encoder for encoding information arranged to be read by the reader; the handpiece being configured to subject the applicator to at least one stimulus selected from: applying heat, applying cold, applying sound or ultrasound, applying a magnetic field, applying electromagnetic radiation, and the handpiece including a treatment module configured to take up a plurality of operating states as a function of the information read from the application;
fastening the applicator, that includes the applicator element carrying the cosmetic or dermatological composition, on the handpiece;
reading, by the reader, information associated with the applicator; and
operating the handpiece as a function of the information read to subject the applicator to the at least one stimulus.

13. The method according to claim 12, wherein the operation of the handpiece is selected in a manner that is entirely automatic once the applicator is in place on the handpiece.

14. The method according to claim 12, wherein the read information determines at least one operating parameter of the handpiece, or an identifier of the applicator and/or the cosmetic or dermatological composition.

15. The method according to claim 14, wherein the read information determines at least one operating parameter of the handpiece selected from a temperature, a processing time or a level of energy.

16. The method according to claim 12, wherein the read information determines whether use of the applicator is still possible and prevents any operation of the handpiece if not.

17. A method of cosmetic or therapeutic treatment, the method comprising:
providing a device for treating human keratinous materials, the device comprising an electrical appliance comprising a handpiece and a reader; and an applicator suitable for being removably fastened on the handpiece and comprising a solid cosmetic composition or a solid dermatological composition for applying to the keratinous materials and at least one encoder for encoding information arranged to be read by the reader;
fastening the applicator, that includes an applicator element carrying the cosmetic or dermatological composition, on the handpiece;
reading, by the reader, information associated with the applicator; and
operating the handpiece as a function of the information read.

18. A method of cosmetic or therapeutic treatment, the method comprising:
providing a device for treating human keratinous materials, the device comprising an electrical appliance comprising a handpiece and a reader; and an applicator suitable for being removably fastened on the handpiece and comprising an applicator element including fibers and/or foam cells suitable for enabling a cosmetic or dermatological composition to be applied on the keratinous materials; and at least one encoder for encoding information arranged to be read by the reader; and the handpiece including a heater module;
fastening the applicator, that includes the applicator element carrying the cosmetic or dermatological composition, on the handpiece;
reading, by the reader, information associated with the applicator; and
operating the handpiece depending on information read by the heater module to heat the applicator to a predefined temperature as a function of the information read.

19. A device for treating human keratinous materials, the device comprising:
an electrical appliance comprising a handpiece and a reader; and
an applicator suitable for being removably fastened on the handpiece and comprising:
i) an applicator element including fibers and/or cells suitable for enabling a cosmetic or dermatological composition to be applied on the keratinous materials;

ii) at least one encoder for encoding information arranged to be read by the reader; and iii) a frame made up of two portions that overlap at least in part and that hold the applicator element between the two portions;

wherein operation of the handpiece depends on the information read, wherein the handpiece is configured to subject the applicator to at least one stimulus selected from: applying heat, applying cold, applying sound or ultrasound, applying a magnetic field, applying electromagnetic radiation, and wherein the handpiece includes a treatment module configured to take up a plurality of operating states as a function of the information read from the applicator.

20. A device for treating human keratinous materials, the device comprising:

an electrical appliance comprising a handpiece and a reader; and an applicator suitable for being removably fastened on the handpiece and comprising:

i) a solid cosmetic composition or a solid dermatological composition for applying to the keratinous materials;

ii) at least one encoder for encoding information arranged to be read by the reader; and iii) an applicator element including a porous fibrous or cellular substrate that is permeable to the cosmetic or dermatological composition, said applicator element being configured to apply the cosmetic or dermatological composition on the keratinous materials;

wherein operation of the handpiece depends on the information read.

* * * * *